(12) United States Patent
Dhar et al.

(10) Patent No.: US 6,974,815 B2
(45) Date of Patent: Dec. 13, 2005

(54) HEXAHYDRO-BENZIMIDAZOLONE COMPOUNDS USEFUL AS ANTI-INFLAMMATORY AGENTS

(75) Inventors: T G. Murali Dhar, Newtown, PA (US); Dominique Potin, Epone (FR); Magali Jeannine Blandine Maillet, Suresnes (FR); Michele Launay, Rueil Malmaison (FR); Eric Antoine Nicolai, Rueil Malmaison (FR); Edwin J. Iwanowicz, San Diego, CA (US)

(73) Assignees: Bristol-Myers Squibb Company, Princeton, NJ (US); Cerep SA, Rueil-Malmaison (FR)

( * ) Notice: Subject to any disclaimer, the term of this patent is extended or adjusted under 35 U.S.C. 154(b) by 186 days.

(21) Appl. No.: 10/681,924

(22) Filed: Oct. 9, 2003

(65) Prior Publication Data

US 2004/0116467 A1 Jun. 17, 2004

Related U.S. Application Data

(60) Provisional application No. 60/417,935, filed on Oct. 11, 2002.

(51) Int. Cl.[7] ................ A61K 31/4188; A61K 31/4184; A61K 31/437; C07D 235/26; C07D 237/26
(52) U.S. Cl. .................. 514/252.06; 514/387; 544/236; 544/265; 544/335; 544/350; 546/118; 548/302.7
(58) Field of Search ....................... 548/302.7; 514/387, 514/252.06; 544/335, 236, 265, 350; 546/118

(56) References Cited

U.S. PATENT DOCUMENTS

| | | | | |
|---|---|---|---|---|
| 3,930,005 | A | * 12/1975 | Wojnar et al. | ......... 514/263.37 |
| 4,925,853 | A | * 5/1990 | Smith et al. | ................. 514/338 |
| 4,925,854 | A | * 5/1990 | Schollkopf et al. | ......... 514/338 |
| 4,933,338 | A | * 6/1990 | Constansa et al. | ........ 514/234.5 |
| 5,021,443 | A | * 6/1991 | Bru-Magniez et al. | ...... 514/394 |
| 5,124,336 | A | * 6/1992 | Bru-Magniez et al. | ...... 514/303 |
| 5,128,359 | A | * 7/1992 | Bru-Magniez et al. | ...... 514/394 |
| 5,182,280 | A | * 1/1993 | Cuberes-Altisent et al. | ...................... 514/254.06 |
| 5,716,594 | A | * 2/1998 | Elmaleh et al. | ............. 424/1.41 |
| 5,922,869 | A | * 7/1999 | Werbitzky et al. | .......... 544/282 |
| 6,350,763 | B1 | 2/2002 | Kelly et al. | |
| 6,436,947 | B1 | * 8/2002 | Borcherding et al. | .... 514/263.4 |
| 6,710,064 | B2 | * 3/2004 | Launay et al. | ............... 514/387 |

FOREIGN PATENT DOCUMENTS

| | | | | |
|---|---|---|---|---|
| EP | | 245637 A | * 11/1987 | .......... A61K/31/43 |
| EP | | 352960 A | * 1/1990 | .......... A61K/31/52 |
| WO | WO 98/39303 | | 9/1998 | |
| WO | WO 99/11258 | | 3/1999 | |
| WO | WO 99/20617 | | 4/1999 | |
| WO | WO 99/20618 | | 4/1999 | |
| WO | WO 99/49856 | | 10/1999 | |
| WO | WO 00/21920 | | 4/2000 | |
| WO | WO 00/39081 | | 7/2000 | |
| WO | WO 00/48989 | | 8/2000 | |
| WO | WO 00/59880 | | 10/2000 | |
| WO | WO 01/06984 | | 2/2001 | |
| WO | WO 01/07044 | | 2/2001 | |
| WO | WO 01/07048 | | 2/2001 | |
| WO | WO 01/07052 | | 2/2001 | |
| WO | WO 01/07440 | | 2/2001 | |
| WO | WO 01/30781 | | 5/2001 | |
| WO | WO 01/51508 | | 7/2001 | |
| WO | WO 01/58853 | | 8/2001 | |
| WO | WO 02/02522 | | 1/2002 | |
| WO | WO 02/02539 | | 1/2002 | |
| WO | WO 02/28832 | | 4/2002 | |
| WO | WO 02/42294 | | 5/2002 | |
| WO | WO 02/44181 | | 6/2002 | |
| WO | WO 02/059114 | | 8/2002 | |

OTHER PUBLICATIONS

Subramanian, P. and Dryhurst, G., "Isolation and characterization of 5-[3'-(7',9'-dimethyluric acid)]-7,9-dimethyl-Δ3,4-isouric acid," J. Electroanalytical Chem., vol. 262(1-2), pp. 281-287 (Apr. 1989) at p. 286 (Scheme 1, compound 3).*

Anderson, M. and Siahaan, T., "Targeting ICAM-1/LFA-1 interaction for controlling autoimmune diseases: designing peptide and small molecule inhibitors," Peptides, vol. 24, pp. 487-501 (2003) at p. 489, col. 1, lines 28-44; and p. 493 (Table 1).*

Yusuf-Makagiansar, H. et al, "Inhibition of LFA-1/ICAM-1 and VLA-4/VCAM-1 as a Therapeutic Approach to Inflammation and Autoimmune Diseases," Medicinal Research Reviews, vol. 22(2), pp. 146-167 (2002) at p. 151, lines 29-48; p. 152, lines 11-14.*

(Continued)

Primary Examiner—Joseph K. McKane
Assistant Examiner—Anthony J. Paviglianiti
(74) Attorney, Agent, or Firm—Laurelee A. Duncan

(57) ABSTRACT

The present invention is directed to compounds having the formula (I):

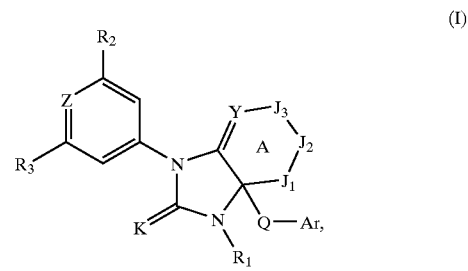

useful in treating inflammatory and immune diseases, in which K is O or S; Q is —C(=O)— or optionally substituted $C_{1-4}$alkylene; Ar is optionally-substituted aryl or heteroaryl; $J_1$, $J_2$, $J_3$, and Y are selected so that ring A is a five-to-six membered optionally-substituted cycloalkenyl or heterocyclo ring having 0 to 2 nitrogen heteroatoms; Z is N or $C(R_9)$; and $R_1$, $R_2$, $R_3$ and $R_9$ are as defined in the specification.

20 Claims, No Drawings

OTHER PUBLICATIONS

Whitcup, S., et al., "Blocking ICAM–1 (CD54) and LFA–1 (CD11a) Inhibits Experimental Allergic Conjunctivitis," Clin. Immun., vol. 93(2), pp. 107–113 (Nov. 1999) at p. 112, line 41 to p. 113 line 2.*

Zameer, A. and Hoffman, S., "Increased ICAM–1 and VCM–1 expression in the brains of autoimmune mice," J. Neuroimmunology, vol. 142, pp. 67–74 (2003) at p. 72, col. 2, line 55 to p. 73, col. 1, line 10.*

Apelt, J., et al., "Beta–Amyloid–associated expression of intercellular adhesion molecule–1 in brain cortical tissue of transgenic Tg2576 mice," Neuroscience Letters, vol. 329, pp. 111–115 (2002) at p. 111, col. 1, lines 4–13; p. 114, col. 1, line 55.*

Tanaka, Y., et al., "Intercellular Adhesion Molecule 1 Discriminates Functionally Different Populations of Human Osteoblasts," J. Bone & Mineral Research, vol. 15(10), pp. 1912–1923 (Oct. 2000), at p. 1922.*

Matsumoto, G., et al., "Essential Role of the Adhesion Receptor LFA–1 for T–Cell–Dependent Fulminant Hepatitis," J. Immunology, vol. 169, pp. 7087–7096 (2002), at p. 7087, col. 2, lines 8–14; p. 7095, lines 25–49.*

Mine, S., et al., "Oxidized low density lipoprotein–induced LFA–1–dependent adhesion and transendothelial migration of monocytes via the protein kinase C pathway," Atherosclerosis, vol. 160, pp. 281–288 (2002), at p. 287, lines 41–54.*

Kapsogeorgou, E., et al., "Activation of epithelial and myoepithelial cells in the salivary glands of patient with Sjogren's syndrome: high expression of ICAM–1 in biopsy specimens," Clin. Exp. Immunology, vol. 124, pp. 126–133 (2001), p. 132, lines 20–25.*

Mileski, W., et al., "Inhibition of CD18–dependent neutrophil adherence reduces organ injury after hemorrhagic shock in primates," Surgery, vol. 108(2), pp. 206–212 (Aug. 1990) at p. 211, col. 2, lines 10–18.*

Yokota, A., et al., "High Avidity State of Leukocyte Function Associated Antigen–1 on Rheumatoid Synovial Fluid T Lymphocytes," J. Immun., vol. 55, pp. 4118–4124 (1995) at p. 4118, col. 2, lines 25–34; p. 4123, lines 55–59.*

Kim, C., et al., "Acyclic Purine Phosphonate Analogues as Antiviral Agents: Synthesis and Structure–Activity Relationships," J. Med. Chem., vol. 33(4) pp. 1207–1213 (1990) at p. 1209, col. 2, lines 1–31.*

Mulligan, M., et al., "Role of Beta1, Beta–2 Integrins and ICAM–1 in Lung Injury after Deposition of IgG and IgA Immune Complexes," J. Immunology, vol. 150(6), pp. 2407–2417 (Mar. 1993), at p. 2414, col. 2, lines 6–10 et seq.*

Mulligan, M., et al., "Compartmentalized Roles for Leukocytic Adhesion Molecules in Lung Inflammatory Injury," J. Immunology, vol. 154; pp. 1350–1363 (1995) at p. 1351, col. 1, lines 7–15; p. 1362, col. 1, lines 3–26.*

Rusznak, C., "Effect of Cigarette Smoke on the Permeability and IL–1–Beta and sICAM–1 Release from Cultured Human Bronchial Epithelial Cells," Am. J. Respir. Cell Mol. Biol., vol. 23, pp. 530–536 (2000) at p. 535, col. 2, lines 12–25.*

Floreani, A., et al., "Smoke and C5a Induce Airway Epithelial Intercellular Adhesion Molecule–1 and Cell Adhesion," Am. J. Respir. Cell Mol. Biol., vol. 29, pp. 472–482 (2003) at p. 478, col. 1, line 56 et seq.*

Noguera, A., et al., "Expression of Adhesion Molecules and G Proteins in Circulating Neutrophils in Chronic Obstructive Pulmonary Disease," Am. J. Respir. Crit. Care Med., vol. 158, pp. 1664–1668 (1998) at p. 1664, col. 1, lines 1–10.*

Takabatake, N., et al., "Impaired systemic cell–mediated immunity and increased susceptibility to acute respiratory tract infections in patients with COPD," Respiratory Medicine, vol. 99, pp. 485–492 (2005) at p. 489, col. 2, lines 46–50.*

Ding, Z., et al., "Relative Contribution of LFA–1 and Mac–1 to Neutrophil Adhesion and Migration," Immunology, vol. 163, pp. 5029–5038 (1999) at p. 5037, col. 2, lines 2–5 and lines 8–21.*

Andrew, D., et al., "Transendothelial migration and trafficking of leukocytes in LFA–1–deficient mice," Eur. J. Immunol., vol. 28, pp. 1959–1969 (1998) at p. 1959, col. 1, line 2 to col. 2, line 13; p. 1966, col. 2, lines 42–53; & p. 1967, lines 1–2.*

Hamaguchi, Y., et al., "Intercellular Adhesion Molecule–1 and L–Selectin Regulate Bleomycin–Induced Lung Fibrosis," Am. J. Path., vol. 161(5) (Nov. 2002) at p. 1608, col. 1, lines 48–53; p. 1616, col. 2, lines 44–54.*

Kuwano, K., et al., "Molecular Mechanisms of Pulmonary Fibrosis and Current Treatment," Current Molecular Medicine, vol. 1(5), pp. 551–573 (2001) at p. 557, col. 2, lines 20–25.*

Agusti, C., et al., "Goblet Cell Degranulation after Antigen Challenge in Sensitized Guinea Pigs," Am. J. Respir. Crit. Care Med., vol. 156, pp. 1253–1258 (1998) at p. 1253, col. 1, lines 1–9; p. 1257, col. 1, lines 1–7.*

Bhatia, M., "Role of inflammatory mediators in the pathophysiology of acute respiratory distress syndrome," Pathol., vol. 202, pp. 145–156 (2004) at p. 148, col. 2, lines 1–16.*

Gauvreau, G., et al., "The effects of an anti–CD11a mAb, efalizumab, on allergen–induced airway responses and airway inflammation in subjects with atopic asthma," J. Allergy Clin. Immunol., vol. 112(2), pp. 331–338 (2003), at p. 332, col. 1, lines 3–14.*

Vincenti, F., "What's in the Pipeline? New Immunosuppressive Drugs in Transplantation," Am. J. Transplantation, vol. 2, pp. 898–903 (2002) at p. 900, col. 1, lines 32–46 and col. 2, lines 1–12.*

Poston, R., et al., "Effects of Humanized Monoclonal Antibody to Rhesus CD11a in Rhesus Monkey Cardiac Allograft Recipients," Transplantation, vol. 69(10), pp. 2005–2013 (May 2000) at p. 2012, col. 1, lines 14–29.*

Dedrick, R., et al., "Adhesion molecules as therapeutic targets for autoimmune diseases and transplant rejection," Expert Opinion Biol. Ther., vol. 3(1), pp. 85–95 (2003) at p. 87, col. 1, lines 1–4 and Table 1; and p. 91, col. 2, lines 1–11 and 30–37.*

Wan, M., et al., "A stain–based inhibitor of lymphocyte function antigen–1 protects against ischemia/reperfusion–induced leukocyte adhesion in the colon," Br. J. Pharmacology, vol. 140(2), pp. 395–401 (2003) at p. 399, lines 8–17; p. 400, lines 2–40.*

Keck, T., et al, "Characterization of ischemia/reperfusion injury after pancreas transplantation and reduction by application of monoclonal antibodies against ICAM–1 in the rat," Surgery, vol. 134, pp. 63–71 (2003) at p. 69, lines 30–33.*

Lavigne, P., et al., "Involvement of ICAM–1 in bone metabolism: a potential target in the treatment of bone diseases?" Expert Opin. Biol. Ther., vol. 5(3), pp. 313–320 (2005) at p. 315, col. 1, lines 1–16 and 44–47; col. 2, lines 4–7 and 30–33.*

Kevil, C. et al., "Loss of LFA–1, but not Mac–1, Protects MRL/MpJ–Fas Mice from Autoimmune Disease," Am. J. Pathol., vol. 165, pp. 609–616 (2004) at p. 615, col. 2, lines 25–35.*

Yung, R., "Mechanisms of Drug–Induced Lupus II. T Cells Overexpressing Lymphocyte Function–associated Antigen 1 Become Autoreactive and Cause a Lupuslike Disease in Syngeneic Mice," J. Clin. Invest., vol. 97, pp. 2866–2871 (1996) at p. 2871, lines 6–8.*

Bernstein, C., "The potential for the beta2 integrin–ICAM–1 adhesion paradigm as a therapeutic target in Crohn's disease," Current Opinions in Anti–Inflammatory & Immunomodulatory Invest. Drugs, vol. 1(4), pp. 308–315 (1999) at p. 311, lines 48–59.*

Tani–Ishii, N., et al., "The role of LFA–1 in osteoclast development induced by co–cultures of mouse bone marrow cells and MC3T3–G2/PA6 cells," J. Periodontal Research, vol. 37, pp. 184–191 (2002) at p. 186, lines 31–38 and Fig. 3.*

Malm, H., et al., "CTLA41G Induces Long–Term Graft Survival of Allogenic Skin Grafts and Totally Inhibits T–Cell Proliferation in LFA–1–Deficient Mice," Transplantation, vol. 73(2), pp. 293–297 (Jan. 2002) at p. 297, lines 9–12.*

Yacyshyn, B., et al., "Double blind, placebo controlled trial of the remission and steriod sparing properties of an ICAM–1 antisense oligodeoxynucleotide, alicaforsen in active steroid dependent Crohn's disease," Gut, vol. 51, pp. 30–36 (2002) at p. 35.*

Glover, J., "Phase I Safety and Pharmacokinetic Profile of an Intercellular Adhesion Molecule–1 Antisense Oligodeoxynucleotide (ISIS 2302)," J. Pharm. Exp. Ther., vol. 282(3), pp. 1173–1180 (1997) at p. 1173, col. 2, lines 1–13; p. 1180, lines 1–4.*

Sondergaard, K., et al., "Soluble Intercellular Adhesion Molecule–1 (sICAM–1) and Soluble Interleukin–2 Receptors (sIL–2R) in Scleroderma Skin," Br. J. Rheum., vol. 37, pp. 304–310 (1998) at p. 309, lines 1–7.*

Mysliwiec, J., et al., "CD11a Expression and soluble ICAM–1 levels in peripheral blood in high–risk and overt type 1 diabetes subjects," Immun. Letters, vol. 70, pp. 69–72 (1999) at p. 71, col. 2, lines 39–41.*

Jaye, D. and Parkos, C., "Neutrophil Migration across intestinal Epithelium," Annals New York Acad. Sci., vol. 915, pp. 151–161 (2000) at p. 151, lines 2–4; p. 156, lines 9–23.*

Dietrich, J., "The adhesion molecule ICAM–1 and its regulation in relation with the blood–brain barrier," J. Neuroimmunology, vol. 128, pp. 58–68 (2002) at p. 62, col. 2, lines 29–38.*

Anderson, D.C. et al., "Leukocyte LFA–1, OKM1, p150,95 deficiency syndrome: functional and biosynthetic studies of three kindreds", Federation Proc., vol. 44, No. 10, pp. 2671–2677 (1985).

Diamond, M.S. et al., "The dynamic regulation of integrin adhesiveness", Current Biology, vol. 4, No. 6, pp. 506–517 (1994).

Górski, A., "The role of cell adhesion molecules in immunopathology", Immunology Today, vol. 15, No. 6, pp. 251–255 (1994).

* cited by examiner

HEXAHYDRO-BENZIMIDAZOLONE COMPOUNDS USEFUL AS ANTI-INFLAMMATORY AGENTS

This application claims benefit of priority from U.S. Provisional Application Ser. No. 60/417,935 filed Oct. 11, 2002, the entirety of which is incorporated herein by reference.

FIELD OF THE INVENTION

The present invention relates to hexahydro-benzimidazolone compounds, pharmaceutical compositions containing them, and methods of using such compounds in treating inflammatory or immune disease.

BACKGROUND OF THE INVENTION

Cells adhere to other cells and to substrates through specific, regulated processes that are critical to various biological functions. The proper functioning of the immune system is dependent upon adhesive interactions and cell migration. A key event in an immune response involves the migration of leukocytes to a disease site. During an inflammatory response, leukocytes are recruited to the site of injury and extravasated by a series of cellular interactions involving cell-cell and cell-substrate adhesion.

One family of molecules that serves an important adhesive function is integrins. Integrins are expressed on cell surfaces and function in cell-cell and cell-substrate adhesion. Integrins are alpha-beta heterodimers: each integrin has an alpha ($\alpha$) subunit non-covalently bound to a beta ($\beta$) subunit. When activated, integrins bind to extracellular ligands and induce adhesion (the expression of integrins on a cell surface alone is inadequate for adhesion—they must be activated to become adhesive). The integrin activation state is transient, such that there is a rapid flux between adhesive and non-adhesive states which is important for cell movement, e.g., a cell is endowed with the ability to rapidly adhere to various cell surfaces and matrices and to migrate among cells and tissue.

There are four known integrins having a $\beta_2$ or CD18 subunit which comprise the CD11/CD18 integrin subfamily, namely, Lymphocyte Function-associated Antigen 1 (LFA-1) (CD11a/CD18 or $\alpha_L\beta_2$); Macrophage Antigen 1 (Mac-1) (CD11b/CD18 or $\alpha_M\beta_2$); p150,95 (CD11c/CD18 or $\alpha_X\beta_2$); and $\alpha_D\beta_2$. The CD11/CD18 family of integrins is also referred to as Leukointegrins as they are expressed on the surface of various leukocyte cells, and they mediate a number of inflammation-related cellular interactions. See Diamond et al., "*The Dynamic Regulation of Integrin Adhesiveness,*" Current Biology, Vol. 4 (1994) at pp. 506–532.

Ligands to LFA-1 and Mac-1 comprise the intercellular adhesion molecule (ICAM) ICAM-1. The primary CD11/CD18 integrin is LFA-1, which also binds with ICAM-2 and ICAM-3. ICAMs are found on endothelium cells, leukocytes, and other cell types, and their interaction with CD11/CD18 integrins is critical to immune system function. The interaction between the CD18 integrins, particularly LFA-1, and ICAMs mediates antigen presentation, T-cell proliferation, and adhesion between the endothelium and activated leukocytes which is necessary for leukocytes to migrate from the circulatory system into tissue. A condition termed "Leukocyte Adhesion Deficiency" has been identified in patients having a deficiency in CD18 integrins. These patients are unable to mount a normal inflammatory or immune response; they suffer from disorders such as recurrent infections, poor wound healing, granulocytosis, progressive periodontitis, and umbilical cord separation. See Anderson et al., "*Leukocyte LFA-1, OKMI, p150.95 Deficiency Syndrome: Functional and Biosynthesis Studies of Three Kindreds,*" Fed. Proc., Vol. 44 (1985), at pp. 2671–2677.

While sufficient levels of CD18 integrins interacting with ICAMs are needed to mount a normal immune response, significant cellular and tissue injury can result in chronic inflammatory states where there is an inappropriate influx of leukocytes to the disease site. Continuous recruitment of leukocytes from blood vessels into inflamed tissue, as in chronic inflammatory states, can perpetuate tissue injury and lead to excessive fibrous repair and autoimmune disease. Thus, inhibition of the interaction between LFA-1 and/or Mac-1 and their ICAMs can be advantageous in treating inflammatory or immune disease. For example, monoclonal antibody blockade of either ICAM or LFA-1 has been shown to prevent the migration of leukocytes into tissue and the subsequent development of inflammatory disease in animal models of rheumatoid arthritis, inflammatory bowel disease, and pulmonary inflammation (e.g., asthma). Knockout mice deficient in ICAMs have reduced susceptibility to induced arthritis, ischemia injury, impaired lung inflammatory responses, and increased tolerance to transplantations (e.g. heart grafts). See Anderson, supra. Antibodies blocking the ICAM-LFA-1 interaction reportedly suppress cardiac allograft rejection and islet cell xenograft rejection in animal models. See Gorski, "*The Role of Cell Adhesion Molecules in Immunopathology,*" Immunology Today, Vol. 15 (1994), at pp. 251–255.

Compounds inhibiting CD18 integrins, ICAMs, and/or the LFA-1:ICAM interaction could potentially demonstrate a wide range of utilities in treating inflammatory or immune diseases. Blocking LFA-1 reportedly inhibits the influx of leukocytes in almost every system, including the skin, peritoneum, synovium, lung, kidney, and heart, and blocking ICAM-1 would be expected to have similar effects. Also, present therapies for many inflammatory and immune diseases have drawbacks. For example, current treatments for asthma include $\beta_2$-agonists, inhaled corticosteroids, and $LTD_4$ antagonists. However, $\beta_2$-agonists have limited efficacy and inhaled corticosteroids raise safety concerns. To treat psoriasis, current therapies include PUVA, methotrexate, cyclosporin A, and topical treatments. The first three of these therapies raise toxicity issues over long-term (e.g., 6–9 month) use, whereas topical treatments have limited efficacy. Additionally, these treatments typically are applied only in response to flares and not as a prophylaxis measure.

Compounds that reportedly inhibit LFA-1/ICAM for use as anti-inflammatory agents include thiadiazole-based compounds (see Intern. Pub. No. WO 99/20,618, "Thiadiazole Amides Useful as Anti-Inflammatory Agents" filed by Pharmacia & Upjohn Co.; and WO 99/20,617, also to Pharmacia and Upjohn). Small molecules that reportedly are antagonists to the binding of ICAMs with CD18 integrins include various benzylamines and 2-bromobenzoyltryptophan compounds (see Intern. Pub. No. WO99/49,856), and 1-(3,5 dichlorophenyl) imidazolidines (see Intern. Pub. No. WO98/39303, "Small Molecules Useful in the Treatment of Inflammatory Disease," filed by Boehringer Ingelheim Pharmaceuticals, Inc. See also Boehringer patent applications WO 01/07052, WO 01/07048, WO 01/07044, WO 01/06984, and WO 01/07440). Hydantoin compounds are disclosed in Intern. Pub. No's WO 00/59880, WO 00/39081, WO 02/02522, WO 02/02539 (all to Abbott Laboratories).

LFA-1 antagonist compounds are also claimed in WO 02/059114 (to Genentech), WO 02/42294 (to Celltech), WO 01/51508 (to Science and Technology corporation), WO 00/21920 and WO 01/58853 (both to Hoffmann-LaRoche), and WO 99/11258, WO 00/48989 and WO 02/28832 (all to Novartis). Hydantoin compounds are disclosed in WO 01/30781 A2 (published May 3, 2001) to Tanabe Seiyaku Co. Ltd, "Inhibitors of $\alpha_L\beta_2$ Mediated Cell Adhesion,". See also, WO 02/44181 (published Jun. 6, 2002), "Hydantoin Compounds Useful as Anti-Inflammatory Agents", to the present assignee and having common inventors herewith.

As may be appreciated, those in the field of pharmaceutical research continue to develop new compounds and compositions for treating inflammatory and immune disease such as inhibitors of Leukointegrins and/or ICAMs. Particularly in the area of immune response, many individuals respond differently to different drugs. Thus, there is an interest in providing consumers not only with pharmaceutical compositions demonstrating increased effectiveness and reduced side-effects but also different structures or mechanisms of action to provide consumers with a choice of options. The instant invention is directed to aryl substituted hexahydro-benzimidazolone compounds that are effective as antagonists of Leukointegrins and/or ICAMs. Each of the patents, patent applications and publications referenced above and hereinafter is incorporated herein by reference.

SUMMARY OF THE INVENTION

The present invention provides compounds useful in treating inflammatory or immune disease having the formula (I):

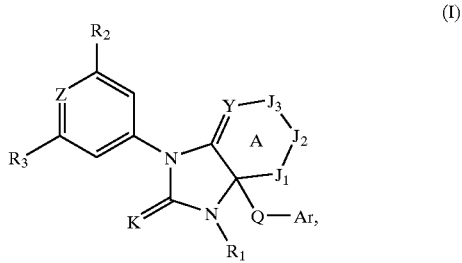

its enantiomers, diastereomers, and pharmaceutically-acceptable salts, hydrates, and prodrugs thereof, in which:
K is O or S;
Q is a bond, —C(=O)— or branched or straight chain $C_{1-4}$alkylene optionally substituted with one to two $R_4$;
Ar is optionally-substituted aryl or heteroaryl;
$J_1$ is a bond, —N($R_5$)—, or —C$R_{6a}R_{7a}$—;
$J_2$ is —N($R_5$)— or —C($R_{6b}R_{7b}$)—;
$J_3$ is —N($R_5$)— or —C($R_{6c}R_{7c}$)—;
provided, however, that only one of $J_1$, $J_2$ and $J_3$ may be —N($R_5$)—, so that ring A is a five-to-six membered cycloalkyl or heterocyclo ring having from 0 to 2 heteroatoms;
Y is N or C($R_8$);
Z is N or C($R_9$);
$R_1$ is selected from hydrogen, alkyl, substituted alkyl, alkenyl, substituted alkenyl, —O$R_{10}$, —N$R_{10}R_{11}$, —C(=O)$R_{10}$, —CO$_2R_{10}$, —C(=O)N$R_{10}R_{11}$, —S(O)$_p$$R_{11a}$, —SO$_2$N$R_{10}R_{11}$, cycloalkyl, heterocyclo, aryl, and heteroaryl;
$R_2$ and $R_3$ are independently selected from hydrogen, halogen, nitro, cyano, alkyl, substituted alkyl, alkenyl, substituted alkenyl, —S$R_{12}$, —O$R_{12}$, —N$R_{12}R_{13}$, —CO$_2R_{12}$, —C(=O)$R_{12}$, —C(=O)N$R_{12}R_{13}$, aryl, heterocyclo, cycloalkyl, and heteroaryl;
$R_4$ is selected from OH, O($C_{1-4}$alkyl), halogen, cyano, CF$_3$, OCF$_3$, NH$_2$, NH($C_{1-4}$alkyl), and N($C_{1-4}$alkyl)$_2$;
$R_5$ is selected from hydrogen, alkyl, substituted alkyl, alkenyl, substituted alkenyl, cyano, —O$R_{14}$, —N$R_{14}R_{15}$, —C(=O)$R_{14}$, —CO$_2R_{14}$, —C(=O)N$R_{14}R_{15}$, —S(O)$_p$$R_{15a}$, —SO$_2$N$R_{14}R_{15}$, aryl, heterocyclo, cycloalkyl, and heteroaryl; or when $R_5$ is joined to atom $J_1$, $J_2$ or $J_3$, $R_5$ may be taken together with one of $R_{6a}$, $R_{6b}$ or $R_{6c}$ attached to an adjacent atom of ring A to form a fused heterocyclo or heteroaryl ring; or when $R_5$ is joined to atom $J_3$, $R_5$ may be taken together with $R_8$ to form a fused heterocyclo ring;
$R_{6a}$, $R_{6b}$, $R_{6c}$, $R_{7a}$, $R_{7b}$, $R_{7c}$ and $R_8$ are independently selected from hydrogen, halogen, alkyl, substituted alkyl, alkenyl, substituted alkenyl, nitro, cyano, —S$R_{16}$, —O$R_{16}$, —N$R_{16}R_{17}$, —C(=O)$R_{16}$, —CO$_2R_{16}$, —C(=O)N$R_{16}R_{17}$, —N$R_{16}$C(=O)$R_{17}$, —N$R_{16}$C(=O)O$R_{17}$, —S(O)$_q$$R_{17a}$, —N$R_{16}$SO$_2R_{17a}$, —SO$_2$N$R_{16}R_{17}$, aryl, heterocyclo, cycloalkyl, and heteroaryl; or $R_{6a}$ with $R_{7a}$, or $R_{6b}$ with $R_{7b}$, or $R_{6c}$ with $R_{7c}$ are taken together to form a keto group (=O) or a spiro cycloalkyl or heterocyclo ring; or $R_{6b}$ taken together with either $R_{6a}$ or $R_{6c}$ may form a fused benzo, cycloalkyl, heterocyclo, or heteroaryl ring; or $R_{6c}$ taken together with $R_8$ may form a fused cycloalkyl or heterocyclo;
$R_9$ is selected from hydrogen, halogen, nitro, cyano, alkyl, substituted alkyl, alkenyl, substituted alkenyl, —S$R_{18}$, —O$R_{18}$, —N$R_{18}R_{19}$, —CO$_2R_{18}$, —C(=O)$R_{18}$, —C(=O)N$R_{18}R_{19}$, aryl, heterocyclo, cycloalkyl, and heteroaryl;
$R_{10}$, $R_{11}$, $R_{12}$, $R_{13}$, $R_{14}$, $R_{15}$, $R_{16}$, $R_{17}$, $R_{18}$, and $R_{19}$ (i) are selected independently of each other from hydrogen, alkyl, substituted alkyl, cycloalkyl, aryl, heteroaryl, and heterocyclo; or (ii) any two of $R_{10}$, $R_{11}$, $R_{12}$, $R_{13}$, $R_{14}$, $R_{15}$, $R_{16}$, $R_{17}$, $R_{18}$, and $R_{19}$ when attached to the same nitrogen atom (as in N$R_{10}R_{11}$, N$R_{12}R_{13}$, N$R_{14}R_{15}$, N$R_{16}R_{17}$, or N$R_{18}R_{19}$) may be taken together to form a heteroaryl or heterocyclo ring, with the remainder of $R_{10}$, $R_{11}$, $R_{12}$, $R_{13}$, $R_{14}$, $R_{15}$, $R_{16}$, $R_{17}$, $R_{18}$, and $R_{19}$ being selected independently from hydrogen, alkyl, substituted alkyl, cycloalkyl, aryl, heteroaryl, and heterocyclo;
$R_{11a}$, $R_{15a}$, and $R_{17a}$ are independently selected from alkyl, substituted alkyl, cycloalkyl, aryl, heteroaryl, and heterocyclo;
p is 1, 2, or 3; and
q is 1, 2, or 3.

The present invention is also directed to pharmaceutical compositions useful in treating immune or inflammatory diseases comprising compounds of formula (I), or pharmaceutically-acceptable salts thereof, and pharmaceutically-acceptable carriers or diluents. The invention further relates to methods of treating immune or inflammatory diseases comprising administering to a patient in need of such treatment a therapeutically-effective amount of a compound according to formula (I).

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy ($C_{0-2}$)alkyl or ($C_{0-2}$)hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $CO_2H$, $CO_2$(alkyl), $C_{3-7}$cycloalkyl, phenyl, benzyl, phenylethyl, napthyl, a four to seven membered heterocylo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of ($C_{1-6}$)alkyl, ($C_{2-6}$)alkenyl, hydroxy, halogen, cyano, nitro, $CF_3$, $O(C_{1-6}alkyl)$, $OCF_3$, $C(=O)H$, $C(=O)(C_{1-6}alkyl)$, $CO_2H$, $CO_2(C_{1-6}alkyl)$, $NHCO_2(C_{1-6}alkyl)$, —$S(C_{1-6}alkyl)$, —$NH_2$, $NH(C_{1-6}alkyl)$, $N(C_{1-6}alkyl)_2$, $N(CH_3)_3^+$, $SO_2(C_{1-6}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$, $C_{3-7}$cycloalkyl, phenyl, benzyl, phenylethyl, phenyloxy, benzyloxy, napthyl, a four to seven membered heterocylo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

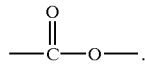

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—$CH_2$—}$_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substitutents as defined above for substituted alkyl groups.

The term "alkoxy" refers to an alkyl group as defined above bonded through an oxygen atom (—O—). The term "substituted alkoxy" includes the groups —O—R, wherein R is a substituted alkyl group as defined above.

The term "thioalkyl" refers to an alkyl group as defined above bonded through a sulfur atom. The term "substituted thioalkyl" includes the groups —S—R, wherein R is a substituted alkyl group as defined above.

The term "alkylamino" refers to an alkyl group as defined above bonded through a nitrogen atom. For example, the term "alkylamino" includes groups such as —NR—$C_{1-12}$alkyl (where R is preferably hydrogen but may include alkyl.) "Aminoalkyl" refers to an amino group bonded through an alkyl, e.g., —$(CH_2)_x$—$NH_2$. "Alkylaminoalkyl" refers to an alkylamino group (i.e., —NHR or NRR) bonded through an alkyl group (e.g., —$(CH_2)_x$—NHR or —$(CH_2)_x$—NRR).

When a subscript is used with reference to an alkoxy, thioalkyl, alkylamino, or aminoalkyl, the subscript refers to the number of carbon atoms that the group may contain in addition to heteroatoms. Thus, for example, monovalent $C_{1-2}$alkylamino includes the groups —NH—$CH_3$, —NH—$CH_2$—$CH_3$, and —N—$(CH_3)_2$.

The term "cycloalkyl" refers to fully saturated and partially unsaturated hydrocarbon rings of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of ($C_{1-4}$)alkyl, ($C_{2-4}$)alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, N($C_{1-4}$alkyl)$_3^+$, SO$_2$($C_{1-4}$alkyl), C(=O)($C_{1-4}$alkylene)NH$_2$, C(=O)($C_{1-4}$alkylene)NH(alkyl), and/or C(=O)($C_{1-4}$alkylene)N($C_{1-4}$alkyl)$_2$.

Accordingly, in compounds of formula (I), the term "cycloalkyl" includes cyclopropyl, cyclobutyl, cyclopentyl, cyclohexyl, cycloheptyl, cyclooctyl, etc., as well as the following ring systems,

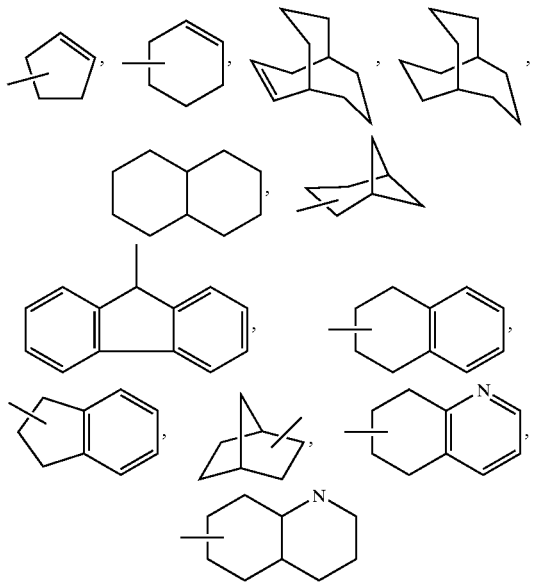

and the like, which optionally may be substituted at any available atoms of the ring(s). Preferred cycloalkyl groups include cyclopropyl, cyclobutyl, cyclopentyl, cyclohexyl,

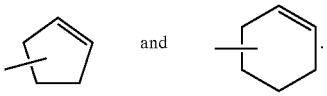

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The term "aryl" refers to phenyl, biphenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, OR$_a$, SR$_a$, (=S), —NR$_a$R$_b$, —N(alkyl)$_3^+$, —NR$_a$SO$_2$, NR$_a$SO$_2$R$_c$, —SO$_2$R$_c$—SO$_2$NR$_a$R$_b$, —SO$_2$NR$_a$C(=O)R$_b$, SO$_3$H, —PO(OH)$_2$, —C(=O)R$_a$, —CO$_2$R$_a$, C(=O)NR$_a$R$_b$, —C(=O)($C_{1-4}$alkylene)NR$_a$R$_b$, —C(=O)NR$_a$(SO$_2$)R$_b$, —CO$_2$($C_{1-4}$alkylene)NR$_a$R$_b$, —NR$_a$C(=O)R$_b$, —NR$_a$CO$_2$R$_b$, —NR$_a$($C_{1-4}$alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of ($C_{1-4}$)alkyl, ($C_{2-4}$)alkenyl, halogen, hydroxy, cyano, nitro, CF$_3$, O($C_{1-4}$alkyl), OCF$_3$, C(=O)H, C(=O)($C_{1-4}$alkyl), CO$_2$H, CO$_2$($C_{1-4}$alkyl), NHCO$_2$($C_{1-4}$alkyl), —S($C_{1-4}$alkyl), —NH$_2$, NH($C_{1-4}$alkyl), N($C_{1-4}$alkyl)$_2$, N($C_{1-4}$alkyl)$_3^+$, SO$_2$($C_{1-4}$alkyl), C(=O)($C_{1-4}$alkylene)NH$_2$, C(=O)($C_{1-4}$alkylene)NH(alkyl), and/or C(=O)($C_{1-4}$alkylene)N($C_{1-4}$alkyl)$_2$.

Thus, examples of aryl groups include:

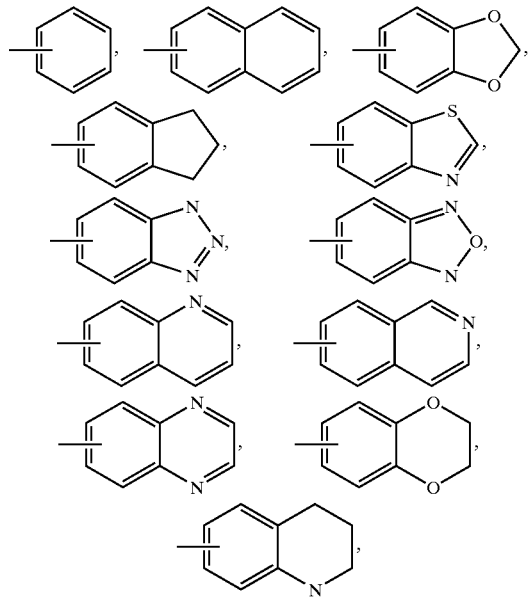

and the like, which optionally may be substituted at any available carbon or nitrogen atom. A preferred aryl group is optionally-substituted phenyl.

The terms "heterocyclo" or "heterocyclic" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)($C_{1-4}$alkylene)NR$_a$R$_b$, —C(=O)NR$_a$(SO$_2$)R$_b$, —CO$_2$($C_{1-4}$alkylene)NR$_a$R$_b$, —NR$_a$C(=O)R$_b$, —NR$_a$CO$_2$R$_b$, —NR$_a$($C_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above. When a heterocyclo is substituted with a further ring, said ring in turn is optionally substituted with one to two of (C$_{1-4}$)alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3$$^+$, SO$_2$(C$_{1-4}$alkyl), C(=O)(C$_{1-4}$alkylene)NH$_2$, C(=O)(C$_{1-4}$alkylene)NH(alkyl), and/or C(=O)(C$_{1-4}$alkylene)N(C$_{1-4}$alkyl)$_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula (I) include

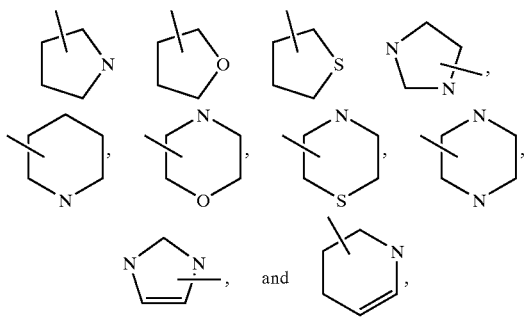

which optionally may be substituted.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, OR$_a$, SR$_a$, (=S), —NR$_a$R$_b$, —N(alkyl)$_3$$^+$, —NR$_a$SO$_2$, —NR$_a$SO$_2$R$_c$, —SO$_2$R$_c$—SO$_2$NR$_a$R$_b$, —SO$_2$NR$_a$C(=O) R$_b$, SO$_3$H, —PO(OH)$_2$, —C(=O)R$_a$, —CO$_2$R$_a$, —C(=O) NR$_a$R$_b$, —C(=O)(C$_{1-4}$alkylene)NR$_a$R$_b$, —C(=O)NR$_a$ (SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above. When a heteroaryl is substituted with a further ring, said ring in turn is optionally substituted with one to two of (C$_{1-4}$)alkyl, (C$_{2-4}$)alkenyl, halogen, hydroxy, cyano, nitro, CF$_3$, O(C$_{1-4}$ alkyl), OCF$_3$, C(=O)H, C(=O)(C$_{1-4}$alkyl), CO$_2$H, CO$_2$ (C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3$$^+$, SO$_2$(C$_{1-4}$ alkyl), C(=O)(C$_{1-4}$alkylene)NH$_2$, C(=O)(C$_{1-4}$alkylene) NH(alkyl), and/or C(=O)(C$_{1-4}$alkylene)N(C$_{1-4}$alkyl)$_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

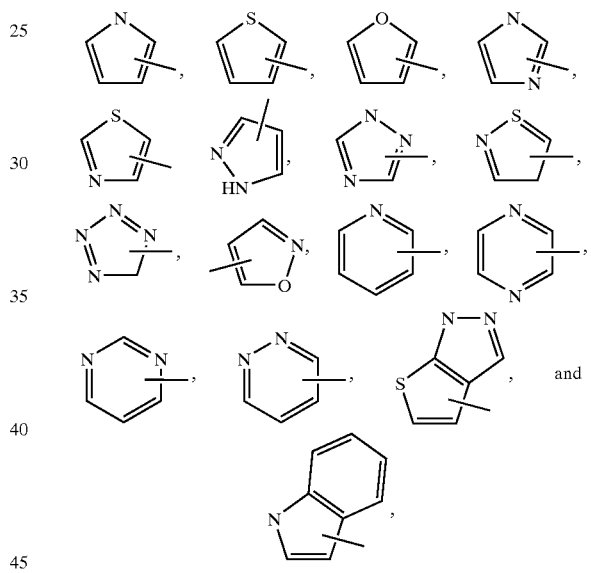

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0–2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable. (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula, (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization. The inventive compounds may be in the free or hydrate form.

Compounds of the Formula (I) may also have prodrug forms. Any compound that will be converted in vivo to provide the bioactive agent, (i.e., the compound for formula I) is a prodrug within the scope and spirit of the invention. Prodrugs and solvates of the inventive compounds are also contemplated. For example, compounds containing a carboxy group can form physiologically hydrolyzable esters which serve as prodrugs by being hydrolyzed in the body to yield formula (I) compounds per se.

Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$ alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

For further examples of prodrug derivatives, see:

a) *Design of Prodrugs*, edited by H. Bundgaard, (Elsevier, 1985) and *Methods in Enzymology*, Vol. 42, pp. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, pp. 113–191 (1991); and c) H. Bundgaard, *Advanced Drug Delivery Reviews*, Vol. 8, pp. 1–38 (1992), each of which is incorporated herein by reference.

It should further be understood that solvates (e.g., hydrates) of the compounds of Formula (I) are also with the scope of the present invention. Methods of solvation are generally known in the art.

Preferred Compounds

Preferred compounds are those having formula (I),

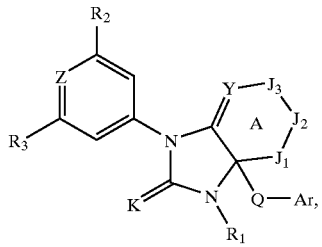

their enantiomers, diastereomers, and pharmaceutically-acceptable salts, hydrates, and prodrug thereof, in which:

K is O;
Q is $C_{1-4}$alkylene;
Ar is optionally-substituted phenyl;
$J_1$ is a bond, —N($R_5$)—, or —C$R_{6a}R_{7a}$—;
$J_2$ is —N($R_5$)— or —C($R_{6b}R_{7b}$)—;
$J_3$ is —N($R_5$)— or —C($R_{6c}R_{7c}$)—;
provided, however, that only one of $J_1$, $J_2$ and $J_3$ may be —N($R_5$)—, so that ring A is a five-to-six membered cycloalkyl or heterocyclo ring having from 0 to 2 heteroatoms;
Y is N or C($R_8$);
Z is N or C($R_9$);
$R_1$ is selected from hydrogen, $C_{1-6}$alkyl, —C(=O)H, —C(=O)($C_{1-6}$alkyl), —CO$_2$H, —CO$_2$($C_{1-6}$alkyl), or $C_{1-6}$alkyl substituted with one to two of hydroxy, —O($C_{1-6}$alkyl), —C(=O)H, —C(=O)($C_{1-6}$alkyl), —CO$_2$H, —CO$_2$($C_{1-6}$alkyl), —C(=O)NH$_2$, —C(=O)NH$_2$, —C(=O)NH($C_{1-4}$alkyl), —C(=O)N($C_{1-4}$alkyl)$_2$, —NH$_2$, —NH($C_{1-4}$alkyl), and —N($C_{1-4}$alkyl)$_2$;
$R_2$ and $R_3$ are selected from halogen, ($C_{1-4}$)alkyl, cyano, halo($C_{1-4}$)alkyl, halo($C_{1-4}$)alkoxy, nitro, phenyloxy, benzyloxy, and phenylthio;
$R_5$ is selected from hydrogen, alkyl, substituted alkyl, alkenyl, substituted alkenyl, cyano, —O$R_{14}$, —N$R_{14}R_{15}$, —C(=O)$R_{14}$, —CO$_2R_{14}$, —C(=O)N$R_{14}R_{15}$, —S(O)$_p$ $R_{15a}$, —SO$_2$N$R_{14}R_{15}$, aryl, heterocyclo, cycloalkyl, and heteroaryl;
$R_{6a}$, $R_{6b}$, $R_{6c}$, $R_{7a}$, $R_{7b}$, $R_{7c}$ and $R_8$ are independently selected from hydrogen, halogen, alkyl, substituted alkyl, alkenyl, substituted alkenyl, nitro, cyano, —S$R_{16}$, —O$R_{16}$, —N$R_{16}R_{17}$, —C(=O)$R_{16}$, —CO$_2R_{16}$, —C(=O)N$R_{16}R_{17}$, —N$R_{16}$C(=O)$R_{17}$, —N$R_{16}$C(=O) O$R_{17}$, —S(O)$_q R_{17a}$, —N$R_{16}$SO$_2R_{17a}$, —SO$_2$N$R_{16}R_{17}$, aryl, heterocyclo, cycloalkyl, and heteroaryl; or $R_{6a}$ with $R_{7a}$, or $R_{6b}$ with $R_{7b}$, or $R_{6c}$ with $R_{7c}$ are taken together to form a keto group (=O);
$R_9$ is selected from hydrogen, halogen, nitro, cyano, alkyl, substituted alkyl, alkenyl, substituted alkenyl, —S$R_{18}$, —O$R_{18}$, —N$R_{18}R_{19}$, —CO$_2R_{18}$, —C(=O)$R_{18}$, —C(=O)N$R_{18}R_{19}$, aryl, heterocyclo, cycloalkyl, and heteroaryl;
$R_{14}$, $R_{15}$, $R_{16}$, $R_{17}$, $R_{18}$, and $R_{19}$ (i) are selected independently of each other from hydrogen, alkyl, substituted alkyl, cycloalkyl, aryl, heteroaryl, and heterocyclo; or (ii) any two of $R_{14}$, $R_{15}$, $R_{16}$, $R_{17}$, $R_{18}$, and $R_{19}$ when attached to the same nitrogen atom (as in N$R_{14}R_{15}$, N$R_{16}R_{17}$, or N$R_{18}R_{19}$) may be taken together to form a heteroaryl or heterocyclo ring, with the remainder of $R_{14}$, $R_{15}$, $R_{16}$, $R_{17}$, $R_{18}$, and $R_{19}$ being selected independently from hydrogen, alkyl, substituted alkyl, cycloalkyl, aryl, heteroaryl, and heterocyclo;
$R_{15a}$, and $R_{17a}$ are independently selected from alkyl, substituted alkyl, cycloalkyl, aryl, heteroaryl, and heterocyclo;
p is 1, 2, or 3; and
q is 1, 2, or 3.

In compounds of formula (I), preferably the groups Q-Ar together form:

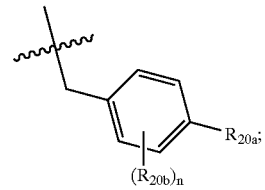

wherein $R_{20a}$ and $R_{20b}$ are independently selected from halogen, $C_{1-4}$alkyl, hydroxy, ($C_{1-4}$)alkoxy, halo($C_{1-4}$)alkyl, halo($C_{1-4}$)alkoxy, cyano, nitro, —CO$_2$H, —C(=O)H, —CO$_2$($C_{1-4}$)alkyl, —C(=O)($C_{1-4}$)alkyl, —C(=O)NH (CH$_2$)$_r$CO$_2$H, —C(=O)NH(CH$_2$)$_r$CO$_2$($C_{1-4}$alkyl), and S(O)$_2$($C_{1-4}$alkyl); or from phenyl, benzyl, phenyloxy, benzyloxy and heteroaryl in turn optionally substituted with one to two of halogen, $C_{1-4}$alkyl, hydroxy, ($C_{1-4}$)alkoxy, halo ($C_{1-4}$)alkyl, halo($C_{1-4}$)alkoxy, cyano, nitro, —NH$_2$, —NH ($C_{1-4}$alkyl), —N($C_{1-4}$alkyl)$_2$, —CO$_2$H, —C(=O)H, —CO$_2$ ($C_{1-4}$)alkyl, and/or —C(=O)($C_{1-4}$)alkyl; or alternatively, two $R_{20b}$ groups join together with each other or one $R_{20b}$ joins together with $R_{20a}$ to form a fused benzo ring; n is 0, 1, or 2; and r is 1, 2, 3, or 4.

More preferred are compounds where Q-Ar form para-substituted benzyl, more preferably para-cyano-benzyl or para-bromo-benzyl.

In compounds of formula (I), preferably $J_1$ is a bond or —CH$R_{6a}$—; $J_2$ is —CH$R_{6b}$—; $J_3$ is —CH$R_{6c}$—; and Y is C($R_8$), wherein $R_{6a}$, $R_{6b}$, $R_{6c}$ and $R_8$ are independently selected from hydrogen, halogen, cyano, —S(alkyl), —S(phenyl), —O(alkyl), phenyloxy, benzyloxy, —O($C_{1-6}$ alkyl), —C(=O)H, —C(=O)($C_{1-6}$alkyl), —CO$_2$H, —CO$_2$ ($C_{1-6}$alkyl), —C(=O)NH$_2$, —C(=O)NH$_2$, —C(=O)NH ($C_{1-4}$alkyl), —C(=O)N($C_{1-4}$alkyl)$_2$, —NH$_2$, —NH($C_{1-4}$ alkyl), —N($C_{1-4}$alkyl)$_2$, or from $C_{1-4}$alkyl, phenyl, four to seven membered heterocyclo, $C_{3-7}$cycloalkyl, and five to six membered heteroaryl, each of which in turn is optionally substituted with one to two groups selected from halogen, cyano, $C_{1-4}$alkyl, hydroxy, trifluoromethyl, trifluoromethoxy, —O($C_{1-6}$alkyl), —C(=O)H, —C(=O) ($C_{1-6}$alkyl), —CO$_2$H, —CO$_2$($C_{1-6}$alkyl), —C(=O)NH$_2$, —C(=O)NH$_2$, —C(=O)NH($C_{1-4}$alkyl), —C(=O)N($C_{1-4}$ alkyl)$_2$, —NH$_2$, —NH($C_{1-4}$alkyl), —N($C_{1-4}$alkyl)$_2$, hydroxy ($C_{1-4}$)alkyl, methoxy($C_{1-4}$)alkyl, ethoxy($C_{1-4}$)alkyl, amino ($C_{1-4}$)alkyl, and halo($C_{1-4}$)alkyl.

More preferred are compounds where $J_1$, $J_2$, and $J_3$ are each —CH$_2$— and Y is CH. Preferably, Z also is CH.

In compounds of formula (I), preferably $R_1$ is hydrogen, $C_{1-6}$alkyl, —C(=O)($C_{1-6}$alkyl), or $C_{1-6}$alkyl substituted with one of —C(=O)H, —C(=O)($C_{1-6}$alkyl), —CO$_2$H, or —CO$_2$($C_{1-6}$alkyl). More preferred are compounds where $R_1$ is hydrogen, methyl, and ethyl, and most preferred are compounds where $R_1$ is methyl.

In compounds of formula (I), preferably $R_2$ and $R_3$ are both halogen, and more preferably, $R_2$ and $R_3$ are both chloro.

Further preferred compounds are those having the formula (Ia),

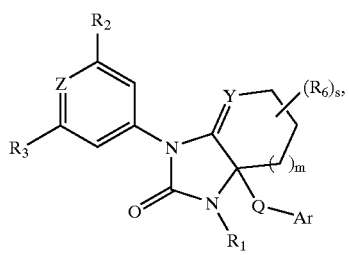
(Ia)

and enantiomers, diastereomers, and pharmaceutically-acceptable salts, hydrates, solvates, and prodrug thereofs, in which:

Q is —(CH$_2$)$_t$—

Ar is phenyl optionally substituted with one to two R$_{20}$;

Y is N or C(R$_8$);

Z is N or C(R$_9$);

R$_1$ is selected from hydrogen, C$_{1-6}$alkyl, —C(=O)H, —C(=O)(C$_{1-6}$alkyl), —CO$_2$H, —CO$_2$(C$_{1-6}$alkyl), or C$_{1-6}$alkyl substituted with one to two of hydroxy, —O(C$_{1-6}$alkyl), —C(=O)H, —C(=O)(C$_{1-6}$alkyl), —CO$_2$H, —CO$_2$(C$_{1-6}$alkyl), —C(=O)NH$_2$, —C(=O)NH$_2$, —C(=O)NH(C$_{1-4}$alkyl), —C(=O)N(C$_{1-4}$alkyl)$_2$, —NH$_2$, —NH(C$_{1-4}$alkyl), and —N(C$_{1-4}$alkyl)$_2$;

R$_2$ and R$_3$ are independently selected from halogen, (C$_{1-4}$) alkyl, cyano, halo(C$_{1-4}$)alkyl, halo(C$_{1-4}$)alkoxy, nitro, phenyloxy, benzyloxy, and phenylthio;

R$_6$ and R$_8$ at each occurrence are independently selected from hydrogen, halogen, cyano, —S(alkyl), —S(phenyl), —O(alkyl), phenyloxy, benzyloxy, —O(C$_{1-6}$alkyl), —C(=O)H, —C(=O)(C$_{1-6}$alkyl), —CO$_2$H, —CO$_2$(C$_{1-6}$alkyl), —C(=O)NH$_2$, —C(=O)NH$_2$, —C(=O)NH(C$_{1-4}$alkyl), —C(=O)N(C$_{1-4}$alkyl)$_2$, —NH$_2$, —NH(C$_{1-4}$alkyl), —N(C$_{1-4}$alkyl)$_2$, or from C$_{1-4}$alkyl, phenyl, four to seven membered heterocyclo, C$_{3-7}$cycloalkyl, and five to six membered heteroaryl, each of which in turn is optionally substituted with one to two groups selected from halogen, cyano, C$_{1-4}$alkyl, hydroxy, trifluoromethyl, trifluoromethoxy, —O(C$_{1-6}$alkyl), —C(=O)H, —C(=O)(C$_{1-6}$alkyl), —CO$_2$H, —CO$_2$(C$_{1-6}$alkyl), —C(=O)NH$_2$, —C(=O)NH$_2$, —C(=O)NH(C$_{1-4}$alkyl), —C(=O)N(C$_{1-4}$alkyl)$_2$, —NH$_2$, —NH(C$_{1-4}$alkyl), —N(C$_{1-4}$alkyl)$_2$, hydroxy(C$_{1-4}$)alkyl, methoxy(C$_{1-4}$)alkyl, ethoxy(C$_{1-4}$)alkyl, amino(C$_{1-4}$)alkyl, and halo(C$_{1-4}$)alkyl; and/or two R$_6$ groups taken together form keto (=O);

R$_9$ is selected from hydrogen, halogen, nitro, cyano, alkyl, substituted alkyl, alkenyl, substituted alkenyl, —S(alkyl), —O(alkyl), S(phenyl), —O(alkyl), phenyloxy, benzyloxy, —O(C$_{1-6}$alkyl), —C(=O)H, —C(=O)(C$_{1-6}$alkyl), —CO$_2$H, —CO$_2$(C$_{1-6}$alkyl), —C(=O)NH$_2$, —C(=O)NH$_2$, —C(=O)NH(C$_{1-4}$alkyl), —C(=O)N(C$_{1-4}$alkyl)$_2$, —NH$_2$, —NH(C$_{1-4}$alkyl), and —N(C$_{1-4}$alkyl)$_2$;

R$_{20}$ at each occurrence is selected from halogen, C$_{1-6}$alkyl, hydroxy, (C$_{1-4}$)alkoxy, (C$_{1-4}$)alkylthio, cyano, nitro, —CO$_2$H, —C(=O)H, —CO$_2$(C$_{1-4}$)alkyl, —C(=O)(C$_{1-4}$)alkyl, —C(=O)NH(CH$_2$)$_r$CO$_2$H, —C(=O)NH(CH$_2$)$_r$CO$_2$(C$_{1-4}$alkyl), S(O)$_2$(C$_{1-4}$alkyl), phenyl, benzyl, phenyloxy, benzyloxy, five to six membered heteroaryl, C$_{3-7}$cycloalkyl, and four to seven membered heterocyclo, wherein, each of the alkyl, alkoxy, and cyclic groups in turn are optionally substituted with one to three of R$_{24}$;

R$_{24}$ is selected from halogen, cyano, nitro, C$_{1-4}$alkyl, hydroxy, trifluoromethyl, trifluoromethoxy, —O(C$_{1-4}$alkyl), —C(=O)H, —C(=O)(C$_{1-6}$alkyl), —CO$_2$H, —CO$_2$(C$_{1-6}$alkyl), —C(=O)NH$_2$, —C(=O)NH$_2$, —C(=O)NH(C$_{1-4}$alkyl), —C(=O)N(C$_{1-4}$alkyl)$_2$, —NH$_2$, —NH(C$_{1-4}$alkyl), —N(C$_{1-4}$alkyl)$_2$, hydroxy(C$_{1-4}$)alkyl, methoxy(C$_{1-4}$)alkyl, ethoxy(C$_{1-4}$)alkyl, amino(C$_{1-4}$)alkyl, and halo(C$_{1-4}$)alkyl;

m is 0 or 1;

r and s are 0, 1, 2, 3 or 4; and t is 1 or 2.

More preferred are compounds having the formula (Ib),

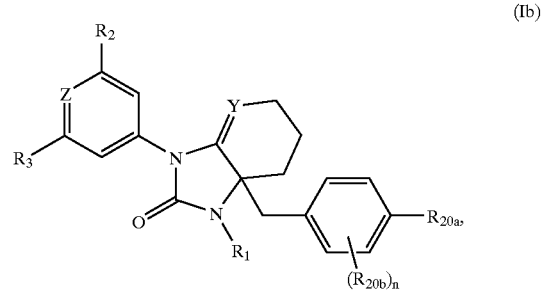
(Ib)

in which R$_1$, R$_2$, R$_3$, Y and Z are selected as recited above for compounds of formula (I), and R$_{20a}$ and R$_{20b}$ are independently selected from halogen, C$_{1-4}$alkyl, hydroxy, (C$_{1-4}$)alkoxy, halo(C$_{1-4}$)alkyl, halo(C$_{1-4}$)alkoxy, cyano, nitro, —CO$_2$H, —C(=O)H, —CO$_2$(C$_{1-4}$)alkyl, —C(=O)(C$_{1-4}$)alkyl, —C(=O)NH(CH$_2$)$_r$CO$_2$H, —C(=O)NH(CH$_2$)$_r$CO$_2$(C$_{1-4}$alkyl), and S(O)$_2$(C$_{1-4}$alkyl); or from phenyl, benzyl, phenyloxy, benzyloxy and heteroaryl in turn optionally substituted with one to two of halogen, C$_{1-4}$alkyl, hydroxy, (C$_{1-4}$)alkoxy, halo(C$_{1-4}$)alkyl, halo(C$_{1-4}$)alkoxy, cyano, nitro, —NH$_2$, —NH(C$_{1-4}$alkyl), —N(C$_{1-4}$alkyl)$_2$, —CO$_2$H, —C(=O)H, —CO$_2$(C$_{1-4}$)alkyl, and/or —C(=O)(C$_{1-4}$)alkyl; or alternatively, two R$_{20b}$ groups join together with each other or one R$_{20b}$ joins together with R$_{20a}$ to form a fused benzo ring; and n is 0, 1 or 2.

Further preferred compounds are those of formula (Ib), as immediately defined above, wherein R$_1$ is C$_{1-4}$ alkyl, R$_2$ and R$_3$ are both halogen (more preferably chlorine), R$_{20a}$ is cyano or halogen, and n is 0.

Most preferred are compounds having the formula,

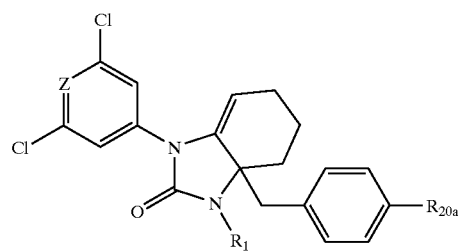

wherein preferably Z is CH, R$_1$ is methyl or ethyl, and R$_{20a}$ is cyano or halogen.

Methods of Preparation

The compounds of the invention may be prepared by the exemplary processes described in the following reaction Schemes A–L. Exemplary reagents and procedures for these reactions appear hereinafter. Starting materials are commercially available or can be readily prepared by one of ordinary skill in the art. For all of the schemes, the groups Z, K, Q, Ar, Y, J$_1$, J$_2$, J$_3$, R$_1$, R$_2$ and R$_3$ are as described herein for a compound of formula (I), unless otherwise indicated.

Groups designated generally as R, R', X, and P as well as solvents, temperatures, pressures, starting materials having the desired groups, and other reaction conditions, may be readily selected as appropriate by one of ordinary skill in the art.

Scheme A:

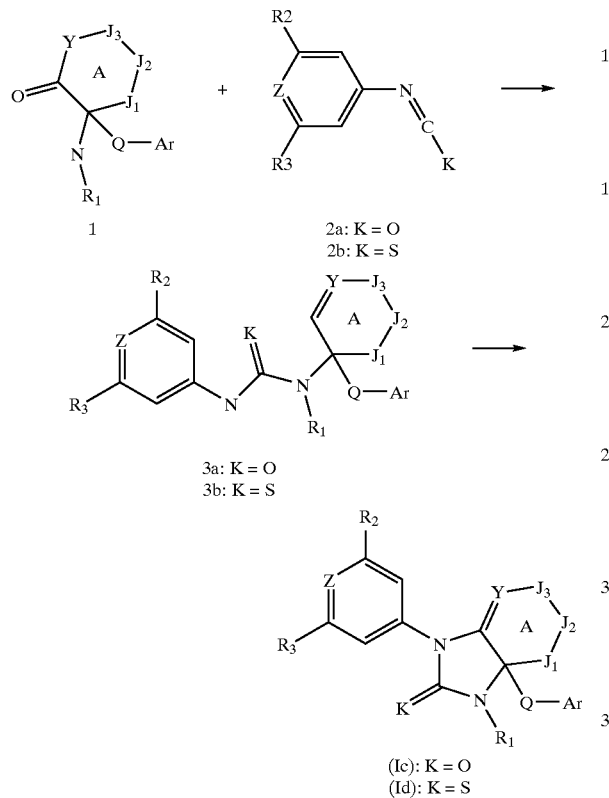

3a: K = O
3b: K = S (Ic): K = O
(Id): K = S

A suitably functionalized amino ketone 1 is reacted with an isocyanate 2a or an isothiocyanate 2b in DCM to yield the ureidoketone 3a or the thioureidoketone 3b, respectively. This intermediate product is then cyclized in an organic solvent such as xylene in the presence of a catalytic amount of base (such as $K_2CO_3$) and molecular sieves at a temperature of 100–140° C. to give the hexahydro-benzimidazolone having the formula (Ic) or hexahydro-benzimidazol-thione having the formula (Id). Compounds of formulae 1, 2a, and 2b are commercially available or can be readily prepared by one skilled in the field as shown in e.g., Demaesle et al., *Tetrahedron Lett.*, Vol. 33 (1992), at pp. 4447–4450; Parcell et al., *J. Org. Chem.*, Vol. 46 (1981), at pp. 5229–5231; or Benati et al., *Tetrahedron.*, Vol. 58 (2002), at pp. 3485–3492.

Scheme B:

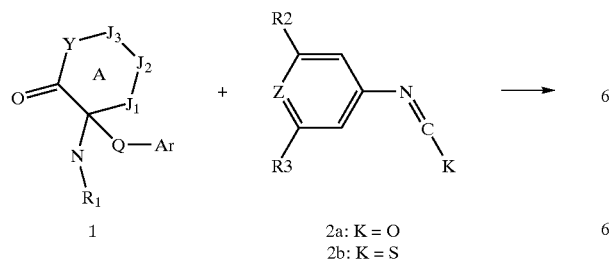

2a: K = O
2b: K = S

-continued

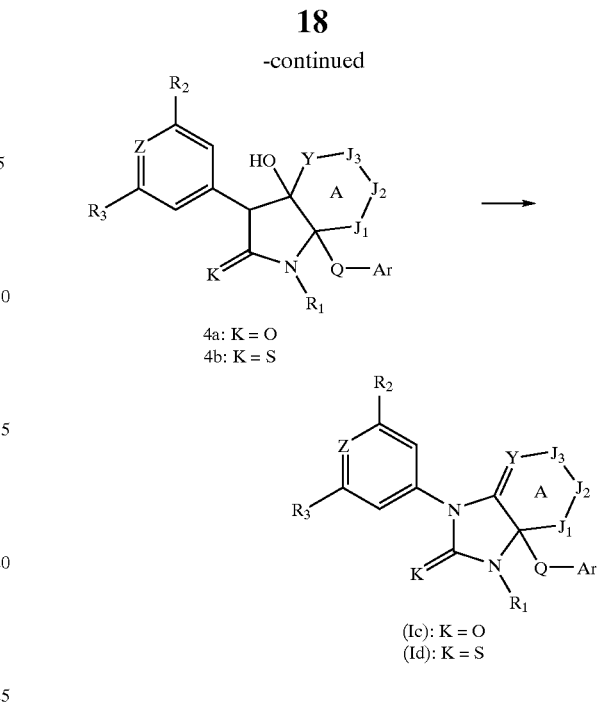

4a: K = O
4b: K = S (Ic): K = O
(Id): K = S

A suitably functionalized amino ketone 1 is reacted with an isocyanate 2a or an isothiocyanate 2b in EtOAc in the presence of a base (such as $Et_3N$, KOH, $K_2CO_3$, $KHCO_3$, $Na_2CO_3$ or $NaHCO_3$), to give after treating with MeOH the hydroxy bicyclic-imidazolone 4a or the hydroxy bicyclic-imidazolthione 4b, respectively. This intermediate product is then dehydrated in an organic solvent (such as toluene) in the presence of a catalytic amount of dehydrating agent (such as PTSA or molecular sieves) at a temperature of 100–140° C. to yield the hexahydro-benzimidazolone having the formula (Ic) or hexahydro-benzimidazol-thione having the formula (Id). See, e.g., Bobowski et al., *J. Heterocycl Chem.*, Vol. 18 (1981), at p. 1179–1187. Compounds of formulae 1, 2a, and 2b are commercially available or can be readily prepared by one skilled in the field as shown in e.g., Demaesle et al., *Tetrahedron Lett.*, Vol. 33 (1992), at pp. 4447–4450; Parcell et al., *J. Org. Chem.*, Vol. 46 (1981), at pp. 5229–5231; or Benati et al., *Tetrahedron.*, Vol. 58 (2002), at pp. 3485–3492.

Scheme C:

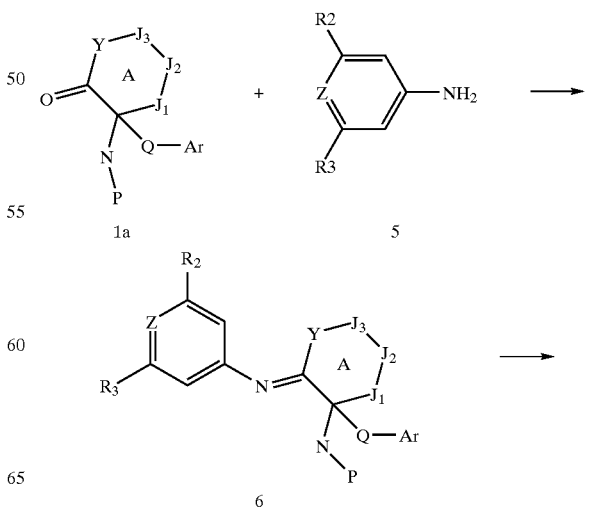

-continued

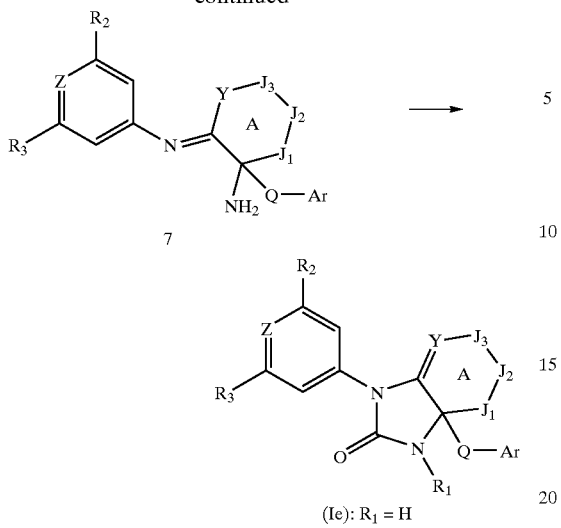

(Ie): R₁ = H

A suitably functionalized Boc-protected amino ketone 1a is heated with an aniline 5 in toluene, to yield the imine 6. This intermediate product is then reacted, after deprotection, with a coupling agent such as triphosgene in an organic solvent (such as DCM) in the presence of base (such as pyridine) to yield the hexahydro-benzimidazolone having the formula (Ie). See, e.g., Rao et al., *Tetrahedron Lett.*, Vol. 34 (1993), at p. 4993. Compounds of formulae 1a and 5 are commercially available or can be readily prepared by one skilled in the field as shown in e.g., Demaesle et al., *Tetrahedron Lett.*, Vol. 33 (1992), at pp. 4447–4450 or Parcell et al., *J. Org. Chem.*, Vol. 46 (1981), at pp. 5229–5231, or Benati et al., *Tetrahedron.*, Vol. 58 (2002), at pp. 3485–3492

Scheme D:

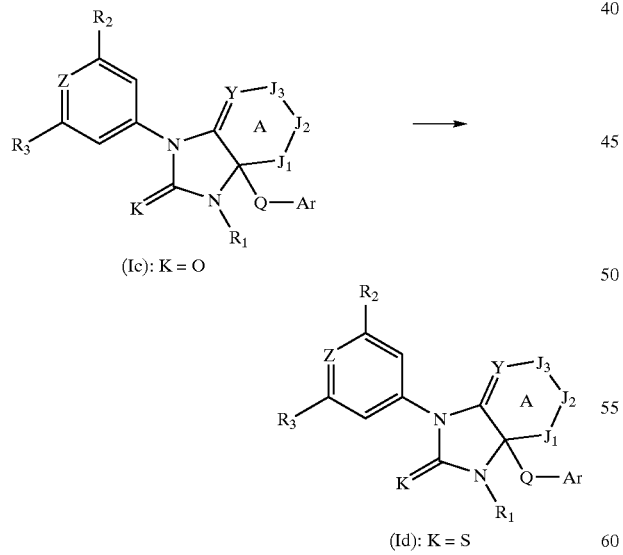

(Ic): K = O (Id): K = S

Treatment of bicyclic imidazolone (Ic) with a reagent such as P₂S₅ or 2,4-bis(4-methoxyphenyl)-1,3-dithia-2,4-diphosphetane-2,4-disulfide (Lawesson's reagent) in an organic solvent such as toluene or dioxane, yields the corresponding hexahydro-benzimidazol-thione having the formula (Id). See, e.g., Rao et al., *Tetrahedron Lett.*, Vol. 34 (1993), at p. 4993.

Scheme E:

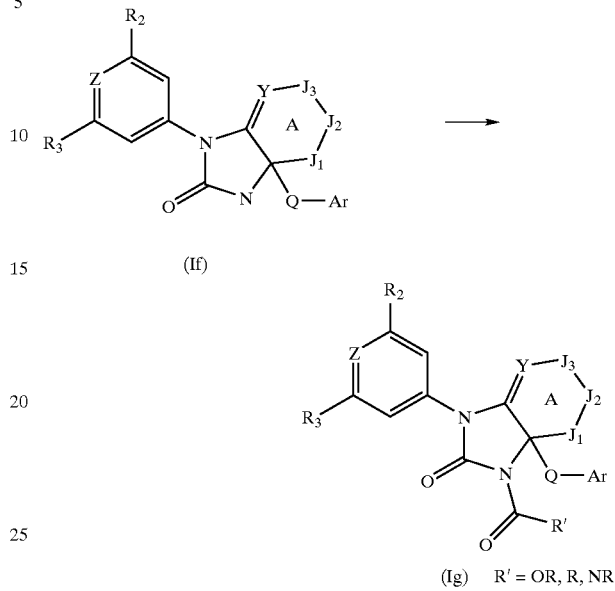

(If)

(Ig)   R' = OR, R, NR

N-acylation of bicyclic imidazolone having the formula (If) can be obtained by treatment with an acylating agent (such as an acyl chloride, an anhydride, a chloroformate or an isocyanate) in an organic solvent (such as THF or acetonitrile) in the presence of a base (such as TEA, DIPEA, DMAP or NaH) to give bicyclic imidazolone having the formula (Ig). See, e.g., Melnyk et al., *Tetrahedron*, Vol. 48 (1992), at pp. 841–850, and Ross et al., *Syn. Commun.*, Vol. 28 (1998), at p. 3877–3884.

Scheme F:

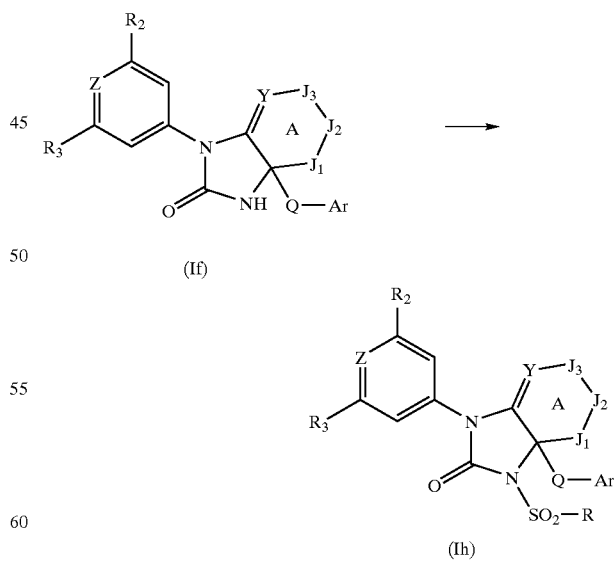

(If)

(Ih)

Sulfonylation of hexahydro-benzimidazolone having the formula (If) is obtained by treatment with a sulfonyl chloride in the presence of a base (such as such as TEA, DIPEA, pyridine or DMAP) in an organic solvent such as toluene to give the desired compounds having the formula (Ih). See, e.g., Yokoyama et al., *Tetrahedron Lett.*, Vol. 39 (1998), at pp. 4847–4850.

Scheme G:

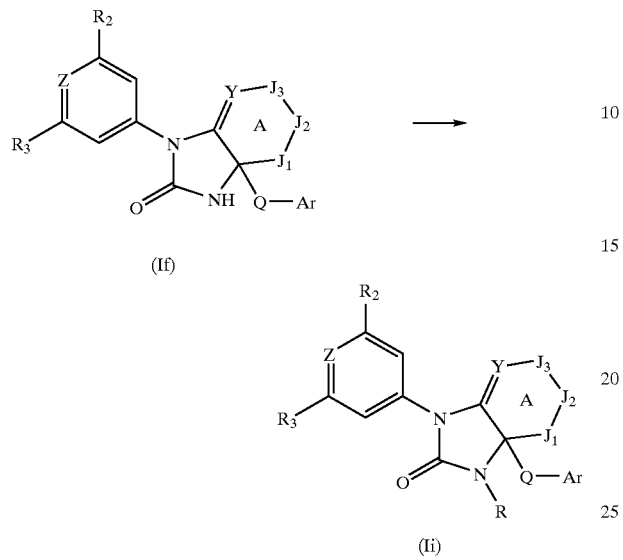

(If)

(Ii)

Bicyclic imidazolone having the formula (If) can be N-alkylated in an aprotic solvent (such as DMF, THF or DMSO) by treatment with one equivalent of a base (such as NaH, NaHMDS, LDA, LIHMDS, KH, KHMDS or tBuOK) followed by addition of a suitable alkylating agent (such as an alkyl iodide, alkyl bromide, alkyl chloride, a tosylate or a mesylate) to yield hexahydro-benzimidazolone having the formula (Ii). See, e.g., Melloni et al., *Farmaco*, Vol. 9 (1991), at pp. 1011–1021.

Scheme H:

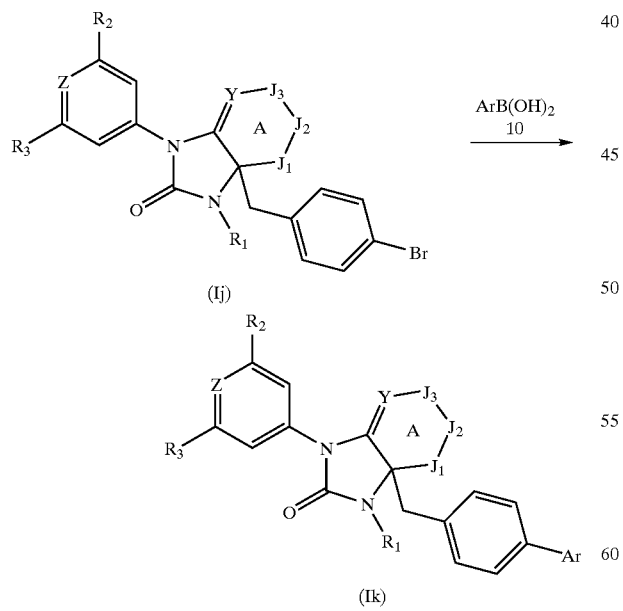

(Ij)

(Ik)

Bromo bicyclic imidazolone having the formula (Ij) can be transformed into biaryl compounds having the formula (Ik) by reaction with an aromatic or heteroaromatic boronic acid 10 in the presence of a palladium catalyst (such as Pd(PPh$_3$)$_4$) and a base (such as K$_2$CO$_3$ or Na$_2$CO$_3$) in an appropriate solvent (such as toluene, DMF, DME or water) under conventional Suzuki coupling conditions. See, e.g., Suzuki et al., *Synth. Commun.*, Vol. 11 (1981), at p. 513.

Scheme I:

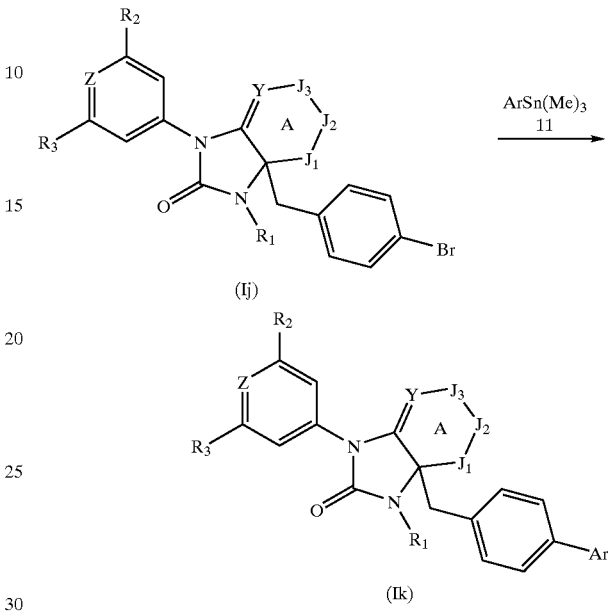

(Ij)

(Ik)

Bromo bicyclic imidazolone having the formula (Ij) can be transformed into biaryl compounds having the formula (Ik) by reaction with an aromatic or heteroaromatic alkyl stannate 11 in the presence of a palladium catalyst (such as Pd(PPh$_3$)$_4$) in an appropriate solvent (such as toluene, DMF, DME or water) under conventional Stille coupling conditions. See, e.g., Yang et al., *Synth. Commun*, Vol. 22; 12; (1992), at pp. 1757–1762.

Scheme J:

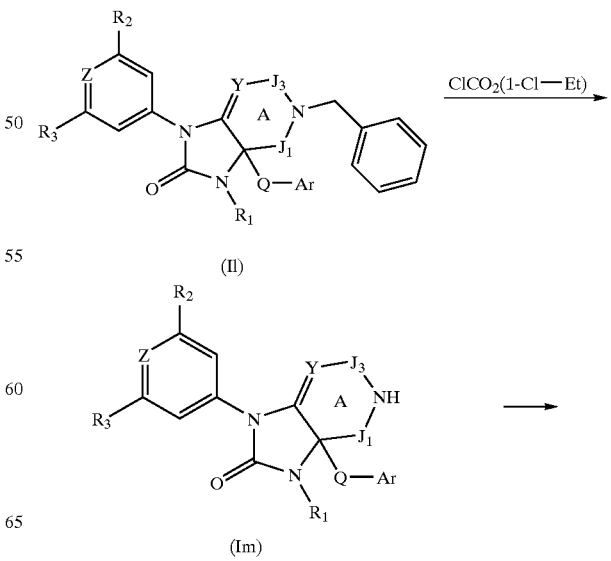

(Il)

(Im)

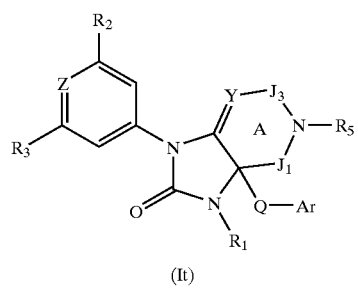

(It)

Bicyclic imidazolone (Il) can be debenzylated using for example 1-chloroethyl chloroformate in a solvent such as dichloromethane or dichloroethane to yield the NH derivative having the formula (Im). This compound can be alkylated either by reaction with an alkyl halide $R_5X$ (for example an alkyl iodide) in a solvent such as acetonitrile or acetone at temperature ranging from room temperature to reflux, or by reaction with an aldehyde in the presence of a reducing agent such as sodium triacetoxy borohydride or sodium cyanoborohydride in a solvent such as acetonitrile or dichloroethane to yield the compound of formula (It).

Scheme K:

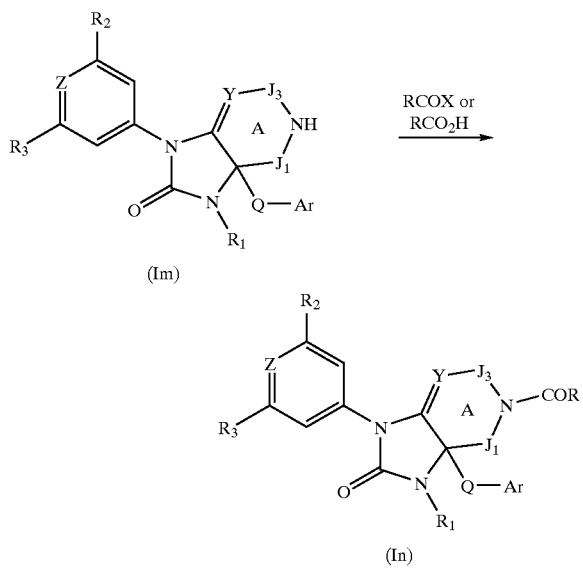

Compounds of formula (Im) can also be acylated with an acyl halide (for example an acyl chloride or acyl bromide) in the presence of an organic base (such as triethylamine or diisopropylethylamine) or an inorganic base (such as sodium carbonate) in a solvent such as dichloromethane at temperature ranging from –15° C. to room temperature to yield the acylated derivative of formula (In). The same compound can also be obtained by reaction with an acid $RCO_2H$ in the presence of a coupling agent such as dicyclohexylcarbodiimide in a solvent such as dichloromethane.

Scheme L:

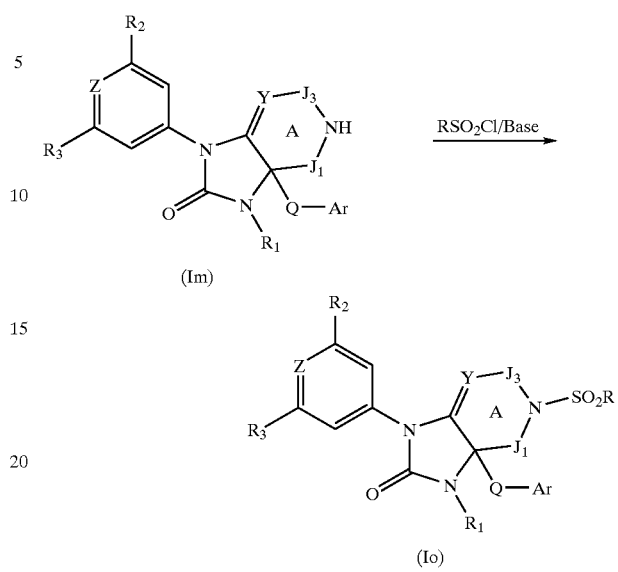

Sulfonamide of formula (Io) can be obtained from compound of formula (Im) by reaction with a sulfonyl halide in the presence of a base (such as triethylamine or sodium carbonate) in a solvent such as dichloromethane or tetrahydrofuran at temperature ranging from –15° C. to room temperature.

Utility

The compounds and compositions of this invention are antagonists and/or inhibitors of LFA-1, Mac-1, and/or ICAMs. They are useful in treating various inflammatory diseases and disorders associated with the action of LFA-1, Mac-1, and/or ICAMs, particularly LFA-1:ICAM-1. The term "Leukointegrin/ICAM-associated condition" is used herein for ease of reference to refer to those diseases or disorders that are associated with the action or levels of LFA-1, Mac-1 and/or ICAM-1, ICAM-2, or ICAM-3. As used herein, the term "treating" includes prophylactic and therapeutic uses and thus includes the alleviation of symptoms of a Leukointegrin/ICAM-associated condition in a patient, the improvement of an ascertainable measurement associated with such a condition, or the prevention of such a condition or its symptoms. The term "patient" refers to a mammal, preferably a human.

In view of their inhibition activity, the compounds may be used to treat conditions involving the activation, co-stimulation, or infiltration of T-cells and/or leukocytes, including without limitation conditions involving the influx of leukocytes in the skin, peritoneum, synovium, lung, kidney, and heart. The inventive compounds may be used to treat conditions resulting from a response of the specific or non-specific immune system in a patient.

Leukointegrin/ICAM-associated conditions that may be treated with the inventive compounds include acute or chronic graft vs host reactions (e.g., pancreatic islet allograft); and acute or chronic transplant rejection (e.g., kidney, liver, heart, lung, pancreas, bone marrow, cornea, small bowel, skin allografts, skin homografts, heterografts, and/or cells derived from such organs). Additionally, the compounds may be used to treat inflammatory conditions including, but not limited to, multiple sclerosis, rheumatoid arthritis, psoriatic arthritis, osteoarthritis, osteoporosis, diabetes (e.g., insulin dependent diabetes mellitus or juvenile onset diabetes), cystic fibrosis, inflammatory bowel disease, irritable bowel syndrome, Crohn's disease, ulcerative colitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome.

The inventive compounds may be used to treat inflammatory conditions of the skin including eczema, atopic dermatitis, contact dermatitis, urticaria, schleroderma, psoriasis, and dermatosis with acute inflammatory components.

The compounds also may also be used to treat allergies and respiratory conditions, including asthma, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, the compounds of the invention may be used to treat autoimmune diseases and/or inflammation associated with autoimmune diseases such as organ-tissue autoimmune diseases (e.g., Raynaud's syndrome), autoimmune thyroiditis, uveitis, systemic lupus erythematosis, Addison's disease, autoimmune polyglandular disease (also known as autoimmune polyglandular syndrome), and Grave's disease.

The compounds of this invention also may be used to treat metastases or as an adjunct to minimize toxicity with cytokine therapy in the treatment of cancers.

The compounds of this invention further have utility in treating hypogonadism, frailty, sexual dysfunction, wasting, such as wasting syndromes associated with cancer and AIDS, and anemia. The compounds further have utility in treating cancers, including but not limited to cancers of the breast, brain, skin, ovary, endometrium, bladder, prostate, lung, colon, lymphatic system, liver and kidney. The inventive compounds are useful for conditions such as hirsutism, acne, seborrhea, alopecia, fibroids, hyperpilosity, cachexia, polycystic ovarian syndrome, anorexia, contraception, drug withdrawal syndrome, pregnancy termination, and benign prostate hypertrophy. The compounds are further useful as antiangiogenic agents. Additionally, the compounds may be useful as inhibitors of protein prenyltransferases, particularly farnesyltransferase and the prenylation of the oncogene protein Ras. As, such, the inventive compounds may potentially be useful for treating and/or preventing the diseases and disorders referred to in WO 01/45704, incorporated herein by reference.

When used as anti-inflammatory agents, the compounds may be administered prior to the onset of, at, or after the initiation of inflammation. When used prophylactically, the compounds are preferably provided in advance of any inflammatory response or symptom (for example, prior to, at, or shortly after the time of an organ or tissue transplant but in advance of any symptoms of organ rejection). Administration of the compounds may prevent or attenuate inflammatory responses or symptoms.

The present invention thus provides methods for treating such conditions as those listed above, comprising administering to a patient in need thereof an effective amount of at least one compound of formula (I) or a salt thereof. Other therapeutic agents such as those described below may be employed in combination with the compounds of formula (I). In the methods of the present invention, such other therapeutic agent(s) may be administered prior to, simultaneously with, or following the administration of the inventive compounds.

The present invention also provides pharmaceutical compositions capable of treating the above-referenced diseases and disorders. The inventive compositions may contain other therapeutic agents and may be formulated, for example, by employing conventional solid or liquid vehicles or diluents, as well as pharmaceutical additives of a type appropriate to the mode of desired administration (for example, excipients, binders, preservatives, stabilizers, flavors, etc.), according to techniques such as those well known in the art of pharmaceutical formulation.

The compounds of formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CAR- BOPOL 934®). Lubricants, glidants, flavors, coloring agents and stabilizers may also be added for ease of fabrication and use.

Exemplary compositions for nasal administration via aerosol or inhalation include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a patient of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and the particular condition sought to be treated and its severity. Preferred subjects for treatment include animals, most preferably mammalian species such as humans, and domestic animals such as dogs, cats, horses, and the like, subject to Leukointegrin/ICAM associated conditions and/or subject to any of the above-referenced diseases and disorders.

The inventive compounds and compositions may be employed alone or in combination with each other and/or other suitable therapeutic agents useful in treating diseases and disorders referenced above, for example, where the second drug has the same or different mechanism of action than the present compounds. Exemplary of such other therapeutic agents include anti-inflammatory agents, antibiotics, anti-viral agents, anti-oxidants, and agents used to treat respiratory conditions such as COPD and asthma.

Examples of suitable other anti-inflammatory agents with which the inventive compounds may be used include aspirin, cromolyn, nedocromil, theophylline, zileuton, zafirlukast, montelukast, pranlukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, Enbrel®, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, cyclooxygenase inhibitors (i.e., COX-1 and/or COX-2 inhibitors such as Naproxen®, Celebrex®, or Vioxx®), CTLA4-Ig agonists/antagonists (LFA29Y), CD40 ligand antagonists, IMPDH inhibitors (such as mycophenolate [CellCept®] and merimepodib), methotrexate (FK506), integrin antagonists (e.g., alpha-4 beta-1, alpha-V-beta-3), cell adhesion inhibitors, interferon gamma antagonists, prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or NF-κB inhibitors (such calphostin, CSAIDs, and quinoxalines as disclosed in U.S. Pat. No. 4,200,750); disassociated steroids; chemokine receptor modulators (including CCR1, CCR2, CCR3, CCR4, and CXCR2 receptor antagonists); secretory and cytosolic phospholipase A2 inhibitors, glucocorticoids, salicylates, nitric oxide, and other immunosuppressants; and nuclear translocation inhibitors, such as deoxyspergualin (DSG).

The inventive compounds may be used in combination with other agents used to treat respiratory conditions such as asthma, COPD, and allergic rhinitis, such as β-adrenergic agonists (such as albuterol, terbutaline, formoterol, salbutamol, salmeterol, bitolterol, pilbuterol, and fenoterol); corticosteroids (such as beclomethasone, triamcinolone, budesonide, fluticasone, flunisolide, dexamethasone, prednisone, and dexamethasone); leukotriene antagonists (e.g., Accolate [Zafirlukast®], and Singulair [Montelukast®]); Muscarinic M3 cholinergic antagonists (e.g., Spiriva®), PDE 4 inhibitors (e.g. rolipram, cilomilast [Ariflo®], piclamilast, or roflumilast), histamine $H_1$ antagonists, Allegra® (fexofenadine), Claritin® (loratidine), and/or Clarinex® (desloratidine).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196–2210 [1997]), PDE2 inhibitors, PDE3 inhibitors (such as revizinone, pimobendan, or olprinone), PDE4 inhibitors (referenced above), PDE7 inhibitors, or other PDE inhibitors such as dipyridamole, cilostazol, sildenafil, denbutyline, theophylline (1,2-dimethylxanthine), ARWFLO™ (i.e., cis-4-cyano-4-[3-(cyclopentyloxy)-4-methoxyphenyl]cyclohexane-1-carboxylic acid), arofyline, C-11294A, CDC-801, BAY-19-8004, cipamfylline, SCH351591, YM-976, PD-189659, mesiopram, pumafentrine, CDC-998, IC-485, and KW-4490.

In view of their usefulness in treating ischemia, the inventive compounds may be used in combination with agents for inhibiting $F_1F_0$-ATPase, including efrapeptin, oligomycin, autovertin B, azide, and compounds described in U.S. patent application Ser. No. 60/339,108, filed Dec. 10, 2001 and assigned to the present assignee; -alpha- or beta-adrenergic blockers (such as propranolol, nadolol, carvedilol, and prazosin), antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); $K^+$ channel modulators such as $I_{Ach}$ inhibitors and inhibitors of the $K_v1$ subfamily of $K^+$ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$ and $P2Y_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

The inventive compounds may also be useful in combination with antiangiogenic agents, such as compounds that are inhibitors of VEGF receptors, or in conjunction with antitumor agents such as paclitaxel, adriamycin, epithilones, cisplatin, and carboplatin. Examples of anticancer and other cytotoxic agents that may be used in combination with the inventive compounds include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416; and prenyl-protein transferase inhibitors as found in WO 97/30992 and WO 98/54966.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Compounds of formula (I), including the compounds described in the examples hereof, have been tested in assay(s) described below and have shown a measurable level of activity as inhibitors of LFA-1 and/or ICAM-1.

Assays

H1-HeLa Adhesion Assay

H1-Hela cells were released from their growth flask using versene (Gibco, Grand Island, N.Y.). Following centrifugation, the cells were resuspended in growth medium: DMEM (Gibco), 10% fetal calf serum (Hyclone, Logan, Utah), 1% Pen-Strep (Gibco), and 1% L-glutamine (Gibco) and plated for growth at 5,000 cells/well in a 96-well plate.

The next day, HSB-2 cells were divided to $2 \times 10^5$/ml in growth medium: RPMI 1640 (Gibco), 10% FCS, 1% Pen-Strep, and 1% L-glutamine. The next day (day #3), the cells were centrifuged at 534×G for 8 minutes, washed, and resuspended in HBSS at $5 \times 10^7$/ml. Calcein-AM, 10 $\mu$M (Molecular Probes, Eugene, Oreg.) and 100 nM phorbol myristate acetate (SIGMA, St. Louis, Mo.) were added to the labeling and activation mix. Following incubation at 37° C. for 30 minutes, ten ml of HBSS was added and the cells centrifuged as above. The cell pellet was then resuspended and counted.

While the HSB-2 cells were labeling, the medium was aspirated from the H1-HeLa cells and the plates washed once with HBSS, followed by the addition of 50 $\mu$l of HBSS. An additional 50 $\mu$l of HBSS containing compound solution, DMSO, or anti-CD18 antibody was then added to each well. To the H1-HeLa cells were added 200,000 HSB-2 cells/well in 100 $\mu$l, followed by incubation in the dark for 30 minutes. The wells were then washed three times to remove the unbound cells. A fluorescence plate reader was then used to determine the number of bound HSB-2 cells. The percent inhibition due to the compound was calculated using the vehicle control as 0% inhibition and the antibody blocked adhesion as 100% inhibition.

HUVEC Adhesion Assay

On day 1, human umbilical vein endothelial cells (HUVEC) (passage 3, Clonetics, San Diego, Calif.) were placed into a T-75 flask containing EGM bulletkit media (Clonetics) for growth.

When the HUVEC were 90% confluent (typically day 4), 96-well tissue culture plates were coated with 100 $\mu$l/well of 2.5 $\mu$g/ml mouse Type IV collagen (Trevigen) diluted in 0.1 M acetic acid. Following incubation for at least three hours, the collagen was removed and the plate washed three times with HBSS (Gibco). The HUVEC flask was trypsinized, and HUVEC were plated on the collagen coated wells at 1250 cells/200 $\mu$l/well for use four days later. Twenty hours prior to use, the medium was removed and cells were stimulated with 200 $\mu$l of 10 nM phorbol myristate acetate (PMA, Sigma, St. Louis, Mo.) in EGM. When the cells were 90% confluent (typically day 8), the PMA-containing medium was removed, the wells were washed with HBSS, and 50 $\mu$l of HBSS was added to the wells. An additional 50 $\mu$l containing compound solution, DMSO or blocking anti-CD18 was then added to each well.

On day 7, HSB-2 cells were then divided to $2 \times 10^5$/ml in RPMI 1640 (Gibco), 10% FCS (Hyclone, Logan, Utah), 1% Pen-Strep (Gibco), and 1% L-glutamine (Gibco). The following day, the cells were centrifuged at 534×G for 8 minutes, washed, and resuspended in HBSS at 5×10⁷/ml. For activation and labeling, calcein-AM, 10 μM (Molecular Probes, Eugene, Oreg.) and 100 nM phorbol myristate acetate (Sigma, St. Louis, Mo.) were added and the cells incubated at 37° C. for 30 minutes. Following the addition of ten ml of HBSS, the cells were centrifuged, resuspended, and counted.

To the HUVEC cells were added 200,000 labeled and activated HSB-2 cells/well in 100 μl, followed by incubation in the dark for 30 minutes. To remove unbound cells, the wells were washed three times with HBSS. A fluorescence plate reader was used to determine the number of HSB-2 cells bound. The percent inhibition due to the compound was calculated with the vehicle control set at 0% inhibition and the antibody-blocked adhesion set at 100% inhibition.

EXAMPLES

The following Examples illustrate embodiments of the inventive compounds and starting materials, and are not intended to limit the scope of the claims. For ease of reference, the following abbreviations are used herein:

Abbreviations bp=boiling point
CH₃CN=acetonitrile
DCC=dicyclohexylcarbodiimide
DCE=dichloroethane
DCM=dichloromethane
DMAP=4-dimethylaminopyridine
DIPEA or DIEA=N,N-diisopropylethylamine
DMF=dimethyl formamide
EDCI=1-3-dimethylaminopropyl)-3-ethylcarbodiimide
HOBT=1-hydroxybenzotriazole
EtOAc=ethyl acetate
EtOH=ethanol
g=gram(s)
HCl=hydrochloric acid
KOH=potassium hydroxide
K₂CO₃=potassium carbonate
l=liter
LiAlH₄=lithium aluminum hydride
MeCN=acetonitrile
MeOH=methanol
MgSO₄=magnesium sulfate
NaH=sodium hydride
Na₂SO₄=sodium sulfate
NaOH=sodium hydroxide
NMP=1-methyl-2-pyrrolidinone
PBr₃=phosphorus tribromide
(Ph₃P)₄Pd=tetrakis(triphenylphosphine)palladium(0)
SOCl₂=thionyl chloride
tBuOMe=t-Butyl methyl ether
TEA=triethylamine
mg=milligram(s)
ml=milliliter
μl=microliter
mmol=millimole
μmol=micromole
mol=mole
mp=melting point
RT=room temperature

Preparation 1

4-[(2-oxocyclohexyl)methyl]-benzonitrile

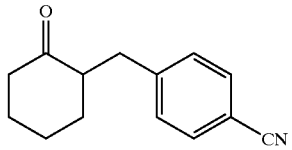

NaI (1 g) was added to a solution of 4-Bromomethyl benzonitrile (12.9 g, 0.066 mol) and 1-(pyrrolidino-1-cyclohexene (10 g, 0.066 mol) in EtOH (150 ml). After 1 night at RT, the reaction mixture was poured into water (500 ml) and extracted twice with EtOAc. The organic phase was washed twice with water, dried over magnesium sulfate and concentrated to yield 4-[(2-oxocyclohexyl)methyl]-benzonitrile (7.06 g) as a yellow oil. ¹H NMR (CDCl₃): 7.60 (2H, d), 7.30 (2H, d), 3.25 (1H, dd), 2.7–2.2 (4H, m), 2.2–1.2 (6H, m).

Preparation 2

4-[[2-(dimethylhydrazono)cyclohexyl]methyl]-benzonitrile

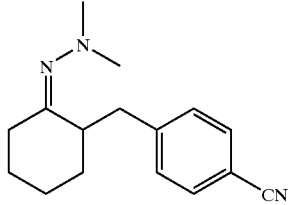

A solution of 4-[(2-oxocyclohexyl)methyl]-benzonitrile (7 g) (0.033 mol) and anhydrous N,N-dimethylhydrazine (9.2 ml) (3,7 eq.) in EtOH (100 ml) was refluxed for 8 h. After cooling, the reaction mixture was concentrated to dryness. The residue was partitioned between tBuOMe and water, the organic phase washed twice with water, dried over magnesium sulfate, and concentrated to yield 4-[[2-(dimethylhydrazono)cyclohexyl]methyl]-benzonitrile (6.1 g) as a orange oil. ¹H NMR (CDCl₃): 7.55 (2H, d), 7.30 (2H, d), 3.15 (1H, dd), 2.9–2.15 (6H, m), 2.3 (6H, s), 1.8–1.3 (4H, m).

Preparation 3

2-[(4-bromophenyl)methyl]-cyclohexanone, dimethylhydrazone

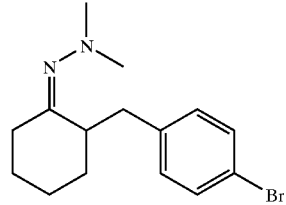

Anhydrous N,N-dimethylhydrazine (17 ml) (3,7 eq.) was quickly poured in a solution of 2-[(4-bromophenyl)methyl]-cyclohexanone (16 g) (0.06 mol) in EtOH (200 ml). The reaction mixture was refluxed for 10 h, then concentrated to dryness. The residue was partitioned between tBuOMe and water, the organic phase washed twice with water, dried over magnesium sulfate and concentrated to yield 2-[(4-bromophenyl)methyl]-cyclohexanone dimethylhydrazone (16 g) as a yellow oil. $^1$H NMR (CDCl$_3$): 7.35 (2H, d), 7.05 (2H, d), 3.05 (1H, dd), 2.4 (6H,s), 2.7–2.2 (4H, m), 1.8–1.3 (6H, m).

Preparation 4

2-[2-[(4-bromophenyl)methyl]-cyclohexylidene]-1,1,1-trimethyl-hydrazinium, Iodide

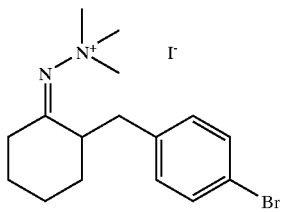

2-[(4-bromophenyl)methyl]-cyclohexanone dimethylhydrazone (16.2 g) (0.052 mol) and methyl iodide (60 ml) were stirred overnight at RT. The precipitate was filtered, washed twice with ethyl ether, then with EtOH, and finally with pentane After drying, 2-[2-[(4-bromophenyl)methyl]-cyclohexylidene]-1,1,1-trimethyl-hydrazinium iodide was obtained as a white solid (11.9 g, mp=173° C.). $^1$H NMR (CDCl$_3$): 7.40 (2H, d), 7.05 (2H, d), 3.7 (9H, s), 3.3–3.1 (1H, m), 3.05 (1H, dd), 2.85–2.45 (3H, m), 2.15–1.4 (6H, m).

Preparation 5

2-[2-[(4-cyanophenyl)methyl]-cyclohexylidene]-1,1,1-trimethyl-hydrazinium, Iodide

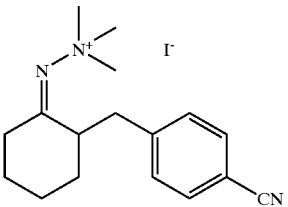

4-[[2-(dimethylhydrazono)cyclohexyl]methyl]-benzonitrile (6.1 g) (0.024 mol) and methyl iodide (35 ml) were stirred overnight at RT. The precipitate was filtered, washed twice with ethyl ether, then with EtOH, and finally with pentane. After drying, 2-[2-[(4-cyanophenyl)methyl]-cyclohexylidene]-1,1,1-trimethyl-hydrazinium iodide was obtained as a white solid (7.8 g, mp=175° C.). $^1$H NMR (CDCl$_3$): 7.55 (2H, d), 7.25 (2H, d), 3.7 (9H, s), 3.3 (1H, m), 3.15 (1H, dd), 2.8–2.5 (3H, m), 2.2–1.4 (6H, m).

Preparation 6

4-(1-amino-2-oxocyclohexylmethyl)-benzonitrile

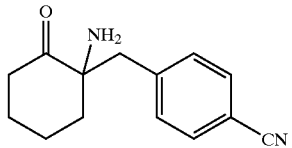

An EtONa/EtOH solution (from Na [0.42 g][0.0185 mol] in EtOH [15 ml]) was heated to 80° C. and 2-[2-[(4-cyanophenyl)methyl]-cyclohexylidene]-1,1,1-trimethyl-hydrazinium iodide (7.8 g) (0.0185 mol) added in portions. After 1 h, the solid has solubilized. The reaction mixture was cooled to RT and a solution of HCl 4M (7.9 ml) carefully added dropwise. After concentration in vacuo, the residue was dissolved in EtOAc, extracted twice with HCl 1N, and the aqueous layer washed with tBuOMe. After basification with an NaOH 1N solution, the aqueous phase was extracted with EtOAc. The organic layer washed with water, dried over magnesium sulfate and concentrated to yield 4-[(1-amino-2-oxocyclohexyl)methyl]-benzonitrile (2.46 g) as a brown oil. $^1$H NMR (CDCl$_3$): 7.55 (2H, d), 7.25 (2H, d), 3.10 (1H, d), 2.85 (1H, d), 2.6 (2H, m), 2.1–1.3 (7H, m).

Preparation 7

2-amino-2-(4-bromo-benzyl)-cyclohexanone

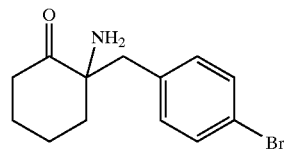

An EtONa/EtOH solution (from Na [0.57 g][0.025 mol] in EtOH [22 ml]) was heated to 80° C. and 2-[2-[(4-bromophenyl)methyl]-cyclohexylidene]-1,1,1-trimethyl-hydrazinium iodide (11.9 g) (0.025 mol) added in portions. After 1 h, the solid solubilized. The reaction mixture was cooled to RT and a solution of HCl 4M (10.7 ml) carefully added dropwise. After concentration in vacuo, the residue was dissolved in EtOAc, extracted twice with HCl 1N, and the aqueous layer washed with tBuOMe. After basification with an NaOH 1N solution, the aqueous phase was extracted with EtOAc. The organic layer was washed with water, dried over magnesium sulfate and concentrated to yield 2-amino-2-(4-bromo-benzyl)-cyclohexanone (3.6 g) as a brown oil. $^1$H NMR (CDCl$_3$): 7.30 (2H, d), 6.95 (2H, d), 2.98 (1H, d), 2.7 (2H, d), 2.65–2.4 (2H, m), 2.1–1.3 (6H, m+NH2).

Preparation 8

1-[1-(4-bromo-benzyl)-2-oxocyclohexyl]-3-(3,5-dichlorophenyl)-urea

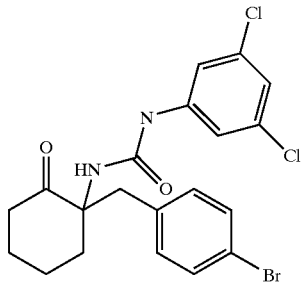

A solution of (3,5-dichorophenyl)-isocyanate (3.1 g) (1.3 eq) in DCM (30 ml) was carefully dropped on 2-amino-2-(4-bromo-benzyl)-cyclohexanone (3.6 g) (0.013 mol) in DCM (35 ml) at 5° C. The temperature was allowed to warm to 20° C., and the mixture was stirred one night. DCM was evaporated in vacuo and the residue purified on $SiO_2$ chromatography (eluent DCM/AcOEt-9.5/0.5) to yied 1-[1-(4-bromo-benzyl)-2-oxocyclohexyl]-3-(3,5-dichlorophenyl)-urea (5.0 g) as a white solid. $^1$H NMR (DMSO-d6): 7.6–7.4 (5H, m), 7.2 (2H, d), 7.05 (1H, bs), 6.6 (1H, bs), 3.0 (1H, d), 2.85 (1H, d), 1.9–1.55 (3H, m), 1.5–1.05 (5H, m).

Preparation 9

N-[1-[(4-cyanophenyl)methyl]-2-oxocyclohexyl]-N'-(3,5-dichlorophenyl)-urea

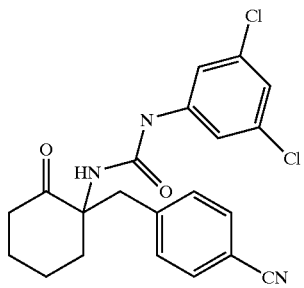

A solution of (3,5-dichorophenyl)-isocyanate (2.7 g) (1.3 eq) in DCM (25 ml) was carefully dropped on 2-amino-2-(4-cyano-benzyl)-cyclohexanone (2.46 g) (0.011 mol) in DCM (25 ml) at 5° C. The temperature was allowed to warm to 20° C., and the mixture was stirred 6 h. DCM was evaporated in vacuo and the residue purified on $SiO_2$ chromatography (eluent DCM/AcOEt-9.5/0.5) to yied 1-[1-(4-cyano-benzyl)-2-oxocyclohexyl]-3-(3,5-dichlorophenyl)-urea (3.76 g) as a white solid. $^1$H NMR (DMSO-d6): 7.75 (2H, d), 7.45 (2H, d), 7.4 (1H, m), 7.35 (2H, m), 7.1 (1H, bs), 6.6 (1H, bs), 3.1 (1H, d), 2.9 (2H, d), 1.9–1.6 (3H, m), 1.5–1.1 (8H, m).

Example 1

3a-(4-Bromo-benzyl)-1-(3,5-dichlorophenyl)-1,3,3a,4,5,6-hexahydro-benzimidazol-2-one

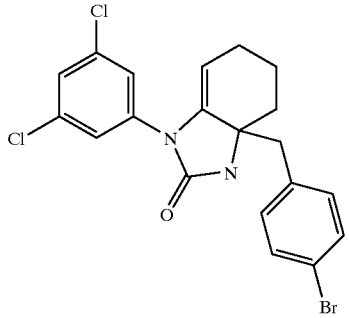

A suspension of 1-[1-(4-bromo-benzyl)-2-oxocyclohexyl]-3-(3,5-dichlorophenyl)-urea (5.0 g) (0.0106 mol), $K_2CO_3$ (3.1 g) (2.1 eq) and molecular sieves 4A (15 g) in xylene (700 ml) was refluxed for 8 h. After cooling, the reaction mixture was filtered on paper, concentrated in vacuo, and the residue purified on $SiO_2$ chromatography (eluent EtOAc/Cyclohexane-3/7) to yield 3a-(4-Bromo-benzyl)-1-(3,5-dichlorophenyl)-1,3,3a,4,5,6-hexahydro-benzimidazol-2-one (3.2 g) as a white solid. $^1$H NMR (CDCl$_3$): 7.45 (2H, d), 7.20 (1H, m), 7.15 (2H, d), 7.05 (2H, m), 4.95 (1H, m), 3.0 (1H, d), 2.90 (1H, d), 2.5–2.1 (2H, m), 2.1–1.8 (3H, m), 1.8–1.6 (1H, m).

Example 2

4-[1-(3,5-Dichlorophenyl)-2-oxo-1,2,3,4,5,6-hexahydro-benzimidazol-3a-ylmethyl]benzonitrile

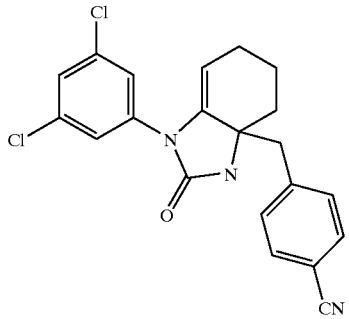

A suspension of 1-[1-(4-cyano-benzyl)-2-oxocyclohexyl]-3-(3,5-dichlorophenyl)-urea (3.7 g) (0.009 mol), $K_2CO_3$ (2.6 g) (2.1 eq) and molecular sieves 4A (10 g) in xylene (500 ml) was refluxed 16 h. After cooling, the reaction mixture was filtered on paper, concentrated in vacuo, and the residue purified on $SiO_2$ chromatography (eluent EtOAc/cyclohexane-3/7) to yield 4-[1-(3,5-Dichlorophenyl)-2-oxo-1,2,3,4,5,6-hexahydro-benzimidazol-3a-ylmethyl]benzonitrile (1.8 g) as a white solid. $^1$H NMR (CDCl$_3$): 7.6 (2H, d), 7.35 (2H, d), 7.15 (1H, m), 6.95 (2H, m), 5.65 (1H, bs), 4.95 (1H, m), 3.1 (1H, d), 2.9 (1H, d), 2.5–2.1 (2H, m), 2.1–1.65 (4H, m).

Example 3

4-[1-(3,5-Dichlorophenyl)-3-methyl-2-oxo-1,2,3,4,5,6-hexahydro-benzimidazol-3a-ylmethyl]benzonitrile

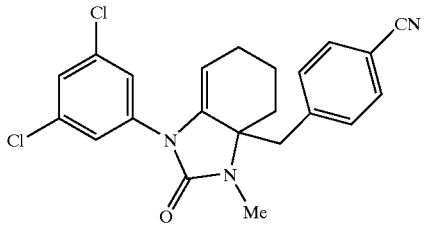

4-[1-(3,5-Dichlorophenyl)-2-oxo-1,2,3,4,5,6-hexahydro-benzimidazol-3a-ylmethyl]benzonitrile (200 mg) (0.5 mmol) in DMF (6 ml) was carefully dropped on a suspension of NaH 60% (24.1 mg) (1.2 eq) in DMF (5 ml) at RT. The reaction mixture was stirred 1 h at RT then methyl iodide (0.095 ml) (3 eq) was added. After one night, the reaction mixture was poured on water and extracted with tBuOMe. The organic layer was washed with water, dried over $Na_2SO_4$, and concentrated to yield a solid which was washed with diisopropyl ether to give 4-[1-(3,5-Dichlorophenyl)-3-methyl-2-oxo-1,2,3,4,5,6-hexahydro-benzimidazol-3a-ylmethyl]benzonitrile (115 mg) as a white solid. $^1$H NMR ($CDCl_3$): 7.55 (2H, d), 7.25 (2H, d), 7.10 (1H, m), 6.75 (2H, m), 4.95 (1H, m), 3.10–3.0 (5H, m), 2.45–1.65 (6H, m).

Example 4

3a-(4-Bromo-benzyl)-1-(3,5-dichlorophenyl)-3-methyl-1,3,3a,4,5,6-hexahydro-benzimidazol-2-one

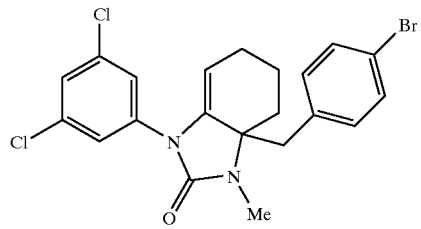

3a-(4-Bromo-benzyl)-1-(3,5-dichlorophenyl)-1,3,3a,4,5,6-hexahydro-benzimidazol-2-one (3.0 g) (0.0066 mol) in DMF (50 ml) was carefully dropped on a suspension of NaH 60% (0.32 g) (1.2 eq) in DMF (20 ml) at RT. The reaction mixture was stirred 1 h at RT then methyl iodide (0.6 ml) (1.5 eq) was added. After one night, the reaction mixture was partitioned between water and tBuOMe. The obtained precipitate was filtered, washed with water and tBuOMe, and dried to give 3a-(4-Bromo-benzyl)-1-(3,5-dichlorophenyl)-3-methyl-1,3,3a,4,5,6-hexahydro-benzimidazol-2-one (1.8 g) as a white solid. $^1$H NMR ($CDCl_3$): 7.39 (2H, d), 7.10 (1H, m), 7.0 (2H, d), 6.77 (2H, m), 4.90 (1H, m), 3.0 (3H, s), 2.95 (2H, s), 2.5–2.2 (2H, m), 2.2–1.9 (3H, m), 1.8–1.6 (1H, m).

Example 5

4-[3-Acetyl-1-(3,5-Dichlorophenyl)-2-oxo-1,2,3,4,5,6-hexahydro-benzimidazol-3a-ylmethyl]benzonitrile

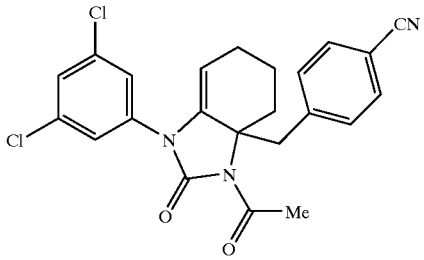

4-[1-(3,5-Dichlorophenyl)-2-oxo-1,2,3,4,5,6-hexahydro-benzimidazol-3a-ylmethyl]benzonitrile (150 mg) (0.38 mmol) in acetic anhydride (5 ml) was refluxed 3 days. After cooling, the reaction mixture was poured on water and extracted with tBuOMe. The organic layer was washed with water, dried over $Na_2SO_4$ and concentrated. The residue was chromatographed over silica gel (DCM/acetone, 97.5/2.5), then HPLC to give 4-[3-Acetyl-1-(3,5-Dichlorophenyl)-2-oxo-1,2,3,4,5,6-hexahydro-benzimidazol-3a-ylmethyl]benzonitrile (13.5 mg) as a white solid. $^1$H NMR ($CDCl_3$): 7.55 (2H, d), 7.3–7.2 (3H, m), 6.70 (2H, m), 4.95 (1H, m), 3.70 (1H, d), 3.05 (1H, m), 2.50 (3H, s), 2.45–2.1 (2H, m), 2.1–1.6 (3H, m).

Example 6

3-Acetyl-3a-(4-Bromo-benzyl)-1-(3,5-dichlorophenyl)-3-methyl-1,3,3a,4,5,6-hexahydro-benzimidazol-2-one

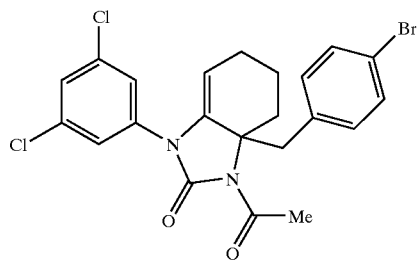

3a-(4-Bromo-benzyl)-1-(3,5-dichlorophenyl)-1,3,3a,4,5,6-hexahydro-benzimidazol-2-one (150 mg) (0.38 mmol) in acetic anhydride (5 ml) was refluxed 3 days. After cooling, the reaction mixture was poured on water and extracted with tBuOMe. The organic layer was washed with water, dried over $Na_2SO_4$ and concentrated. The residue was chromatographed over silica gel (DCM/acetone 97.5/2.5), then HPLC to give 3-Acetyl-3a-(4-Bromo-benzyl)-1-(3,5-dichlorophenyl)-3-methyl-1,3,3a,4,5,6-hexahydro-benzimidazol-2-one (13.5 mg) as a white solid. $^1$H NMR ($CDCl_3$): 7.40 (2H, d), 7.25 (1H, m), 6.98 (2H, d), 6.75 (2H, m), 4.90 (1H, m), 3.55 (1H, d), 3.05–2.9 (2H, m), 2.55 (3H, s), 2.9–2.7 (2H, m), 2.1–1.7 (3H, m).

Example 7

4-[1-(3,5-Dichlorophenyl)-3-ethyl-2-oxo-1,2,3,4,5,6-hexahydro-benzimidazol-3a-ylmethyl]benzonitrile

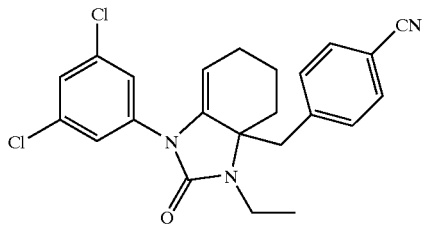

4-[1-(3,5-Dichlorophenyl)-2-oxo-1,2,3,4,5,6-hexahydro-benzimidazol-3a-ylmethyl]benzonitrile (150 mg) (0.38 mmol) in DMF (5 ml) was carefully dropped on a suspension of NaH 60% (18.2 mg) (1.2 eq) in DMF (5 ml) at RT. The reaction mixture was stirred 1 h at RT, then ethyl iodide (0.046 ml) (1.5 eq) was added. After one night, the reaction mixture was poured on water and extracted with tBuOMe. The organic layer was washed with water, dried over $Na_2SO_4$ and concentrated to yield a solid which was purified by HPLC to give 4-[1-(3,5-Dichlorophenyl)-3-ethyl-2-oxo-1,2,3,4,5,6-hexahydro-benzimidazol-3a-ylmethyl]benzonitrile (18.2 mg) as a white solid. $^1$H NMR ($CDCl_3$):. 7.55 (2H, d), 7.25 (2H, d), 7.10 (1H, m), 6.80 (2H, m), 4.95 (1H, m), 3.75 (1H, m), 3.15 (1H, m), 3.0 (2H, s), 2.5–1.7 (6H, m), 1.25 (3H, t).

Example 8

[7a-(4-Cyano-benzyl)-3-(3,5-Dichlorophenyl)-2-oxo-2,3,5,6,7,7a-hexahydro-benzimidazol-3a-yl]-acetic acid ethyl ester

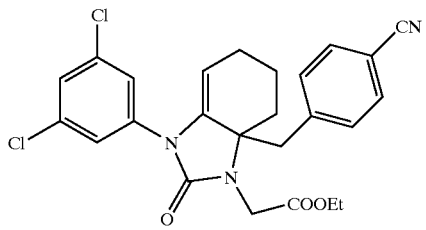

4-[1-(3,5-Dichlorophenyl)-2-oxo-1,2,3,4,5,6-hexahydro-benzimidazol-3a-ylmethyl]benzonitrile (150 mg) (0.38 mmol) in DMF (5 ml) was carefully dropped on a suspension of NaH 60% (18.2 mg) (1.2 eq) in DMF (5 ml) at RT. The reaction mixture was stirred for 1 h at RT, then ethyl bromoacetate (0.052 ml) (1.2 eq) was added. After one night, the reaction mixture was poured on water and extracted with tBuOMe. The organic layer was washed with water, dried over $Na_2SO_4$ and concentrated. The residue was purified on $SiO_2$ chromatography (eluent EtOAc/cyclohexane—2/8) to give [7a-(4-Cyano-benzyl)-3-(3,5-Dichlorophenyl)-2-oxo-2,3,5,6,7,7a-hexahydro-benzimidazol-3a-yl]-acetic acid ethyl ester (46.5 mg) as a white solid. $^1$H NMR ($CDCl_3$): 7.55 (2H, d), 7.25 (2H, d), 7.1 (1H, m), 6.8 (2H, m), 5.0 (1H, m), 4.45 (1H, d), 4.2 (2H, q), 3.75 (1H, d), 3.05 (1H, d), 2.90 (1H, d), 2.5–2.1 (2H, m), 2.1–1.8 (4H, m), 1.25 (3H, t).

Example 9

[7a-(4-Cyano-benzyl)-3-(3,5-Dichlorophenyl)-2-oxo-2,3,5,6,7,7a-hexahydro-benzimidazol-3a-yl]-acetic acid

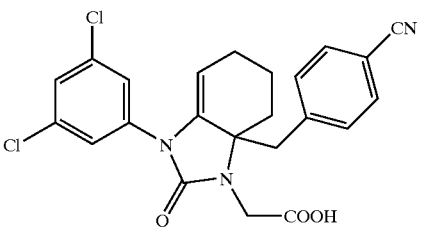

[7a-(4-Cyano-benzyl)-3-(3,5-Dichlorophenyl)-2-oxo-2,3,5,6,7,7a-hexahydro-benzimidazol-3a-yl]-acetic acid ethyl ester (34 mg) (0.07 mmol) and LiOH (3.0 mg) (1.1 eq) in a 1:1 mixture of MeOH/$H_2O$ (4 ml) (5 ml) were stirred 4 days. The reaction mixture was acidified with an aqueous solution of HCl 1N, then concentrated. The residue was purified on HPLC to give [7a-(4-Cyano-benzyl)-3-(3,5-Dichlorophenyl)-2-oxo-2,3,5,6,7,7a-hexahydro-benzimidazol-3a-yl]-acetic acid (3.9 mg) as a white solid. $^1$H NMR ($CDCl_3$): 7.55 (2H, d), 7.25 (2H, d), 7.15 (1H, m), 6.75 (2H, m), 5.0 (1H, m), 4.45 (1H, d), 3.83 (1H, d), 3.05 (1H, d), 2.9 (1H, d), 2.5–2.1 (2H, m), 2.1–1.8 (4H, m).

Example 10

[7a-(4-Bromo-benzyl)-3-(3,5-Dichlorophenyl)-2-oxo-2,3,5,6,7,7a-hexahydro-benzimidazol-3a-yl]-acetic acid ethyl ester

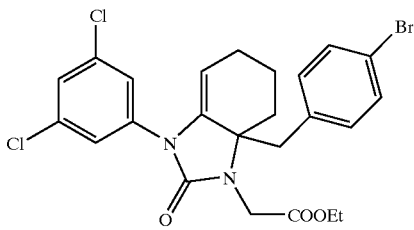

3a-(4-Bromo-benzyl)-1-(3,5-dichlorophenyl)-1,3,3a,4,5,6-hexahydro-benzimidazol-2-one (190 mg) (0.42 mmol) in DMF (5 ml) was carefully dropped on a suspension of NaH 60% (20.2 mg) (1.2 eq) in DMF (5 ml) at RT. The reaction mixture was stirred 1 h at RT, then ethyl bromoacetate (0.094 ml) (2.0 eq) was added. After one night at RT, the mixture was heated to 100° C. for 8 h, then the reaction mixture was poured on water and extracted with tBuOMe. The organic layer was washed with water, dried over $Na_2SO_4$ and concentrated. The residue was purified on $SiO_2$ chromatography (eluent EtOAc/cyclohexane—1/10) to give [7a-(4-Bromo-benzyl)-3-(3,5-dichlorophenyl)-2-oxo-2,3,5,6,7,7a-hexahydro-benzimidazol-3a-yl]-acetic acid ethyl ester (30.2 mg) as a yellow oil. $^1$H NMR ($CDCl_3$): 7.35 (2H, d), 7.10 (1H, m), 6.95 (2H, m), 6.8 (2H, m), 4.95 (1H, m), 4.45 (1H, d), 4.2 (2H, q), 3.7 (1H, d), 2.9 (1H, d), 2.8 (1H, d), 2.45–2.1 (2H, m), 2.0–1.8 (4H, m), 1.25 (3H, t).

Example 11

6-[7a-(4-Cyano-benzyl)-3-(3,5-Dichlorophenyl)-2-oxo-2,3,5,6,7,7a-hexahydro-benzimidazol-3a-yl]-hexanoic acid ethyl ester

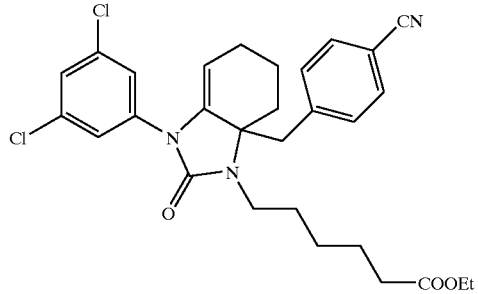

4-[1-(3,5-Dichlorophenyl)-2-oxo-1,2,3,4,5,6-hexahydro-benzimidazol-3a-ylmethyl]benzonitrile (500 mg) (1.25 mmol) in DMF (20 ml) was carefully dropped on a suspension of NaH 60% (65 mg) (1.3 eq) in DMF (10 ml) at RT. The reaction mixture was stirred 1 h at RT, then ethyl hexanoate (0.27 ml) (1.2 eq) was added. After 3 h, the reaction mixture was poured on water and extracted with tBuOMe. The organic layer was washed with water, dried over $Na_2SO_4$ and concentrated. The residue was purified on $SiO_2$ chromatography (eluent EtOAc/cyclohexane—2/8) to give 6-[7a-(4-Cyano-benzyl)-3-(3,5-Dichlorophenyl)-2-oxo-2,3,5,6,7,7a-hexahydro-benzimidazol-3a-yl]-hexanoic acid ethyl ester (200 mg) as an oil. $^1$H NMR ($CDCl_3$): 7.55 (2H, d), 7.25 (2H, d), 7.1 (1H, m), 6.75 (2H, m), 4.95 (1H, m), 4.15 (2H, q), 3.7 (1H, m), 3.1 (1H, m), 3.0 (2H, s), 2.35 (2H, m), 2.2–1.3 (12H, m), 1.23 (3H, t).

Example 12

1-(3,5-Dichlorophenyl)-3-methyl-3a-(4-pyrimidin-5-yl-benzyl)-1,3,3a,4,5,6-hexahydro-benzimidazol-2-one

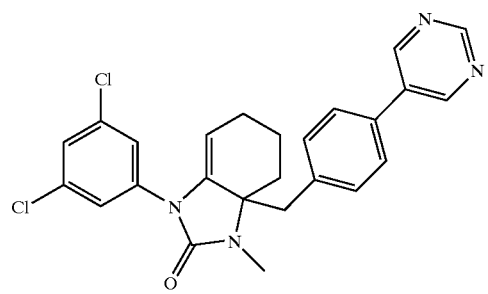

To 3a-(4-Bromo-benzyl)-1-(3,5-dichlorophenyl)-3-methyl-1,3,3a,4,5,6-hexahydro-benzimidazol-2-one (1.0 g) (0.002 mol) and 4-pyrimidinyl-trimethyl stannane (0.73 g) (1.5 eq) in dry toluene (20 ml) was added tetrakis (triphenylphosphine) palladium (347 mg) (0.15 eq). The reaction mixture was refluxed 11 h. After cooling, it was filtered on paper and the filtrate concentrated. The residue was purified on $SiO_2$ chromatography (eluent DCM/acetone—9/1) then HPLC to give 1-(3,5-Dichlorophenyl)-3-methyl-3a-(4-pyrimidin-5-yl-benzyl)-1,3,3a,4,5,6-hexahydro-benzimidazol-2-one (15 mg) as an off-white solid. $^1$H NMR ($CDCl_3$): 9.15 (1H, s), 8.85 (2H, s), 7.48 (2H, d), 7.26 (2H, d), 7.02 (1H, m), 6.73 (2H, m), 4.93 (1H, m), 3.05 (3H, s), 2.98 (2H, dd), 2.5–1.9 (5H, m), 175 (1H, m).

We claim:
1. A compound of formula (I),

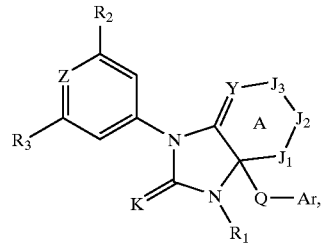

its enantiomers, diastereomers, or a pharmaceutically-acceptable salt, hydrate, or prodrug thereof, in which:

K is O or S;

Q is a bond, —C(=O)— or branched or straight chain $C_{1-4}$alkylene optionally substituted with one to two $R_4$;

Ar is optionally-substituted aryl or heteroaryl;

$J_1$ is —N($R_5$)—, or —C$R_{6a}R_{7a}$—;

$J_2$ is —N($R_5$)— or —C($R_{6b}R_{7b}$)—;

$J_3$ is —N($R_5$)— or —C($R_{6c}R_{7c}$)—;

provided, however, that only one of $J_1$, $J_2$ and $J_3$ may be —N($R_5$)—, so that ring A is a six membered cycloalkyl or heterocyclo ring having from 0 to 2 heteroatoms;

Y is N or C($R_8$);

Z is N or C($R_9$);

$R_1$ is selected from hydrogen, alkyl, substituted alkyl, alkenyl, substituted alkenyl, —$OR_{10}$, —$NR_{10}R_{11}$, —C(=O)$R_{10}$, —$CO_2R_{10}$, —C(=O)$NR_{10}R_{11}$, —S(O)$_pR_{11a}$, —$SO_2NR_{10}R_{11}$, cycloalkyl, heterocyclo, aryl, and heteroaryl;

$R_2$ and $R_3$ are independently selected from hydrogen, halogen, nitro, cyano, alkyl, substituted alkyl, alkenyl, substituted alkenyl, —$SR_{12}$, —$OR_{12}$, —$NR_{12}R_{13}$, —$CO_2R_{12}$, —C(=O)$R_{12}$, —C(=O)$NR_{12}R_{13}$, aryl, heterocyclo, cycloalkyl, and heteroaryl;

$R_4$ is selected from OH, O($C_{1-4}$alkyl), halogen, cyano, $CF_3$, $OCF_3$, $NH_2$, NH($C_{1-4}$alkyl), and N($C_{1-4}$alkyl)$_2$;

$R_5$ is selected from hydrogen, alkyl, substituted alkyl, alkenyl, substituted alkenyl, cyano, —$OR_{14}$, —$NR_{14}R_{15}$, —C(=O)$R_{14}$, —$CO_2R_{14}$, —C(=O)$NR_{14}R_{15}$, —S(O)$_pR_{15a}$, —$SO_2NR_{14}R_{15}$, aryl, heterocyclo, cycloalkyl, and heteroaryl; or when $R_5$ is joined to atom $J_1$, $J_2$ or $J_3$, $R_5$ may be taken together with one of $R_{6a}$, $R_{6b}$ or $R_{6c}$ attached to an adjacent atom of ring A to form a fused heterocyclo or heteroaryl ring; or when $R_5$ is joined to atom $J_3$, $R_5$ may be taken together with $R_8$ to form a fused heterocyclo ring;

$R_{6a}$, $R_{6b}$, $R_{6c}$, $R_{7a}$, $R_{7b}$, $R_{7c}$ and $R_8$ are independently selected from hydrogen, halogen, alkyl, substituted alkyl, alkenyl, substituted alkenyl, nitro, cyano, —$SR_{16}$, —$OR_{16}$, —$NR_{16}R_{17}$, —C(=O)$R_{16}$, —$CO_2R_{16}$, —C(=O)$NR_{16}R_{17}$, —$NR_{16}C(=O)R_{17}$, —$NR_{16}C(=O)OR_{17}$, —S(O)$_qR_{17a}$, —$NR_{16}SO_2R_{17a}$, —$SO_2NR_{16}R_{17}$, aryl, heterocyclo, cycloalkyl, and heteroaryl; or $R_{6a}$ with $R_{7a}$, or $R_{6b}$ with $R_{7b}$, or $R_{6c}$ with $R_{7c}$ are taken together to form a keto group (=O) or a spiro cycloalkyl or heterocyclo ring; or $R_{6b}$ taken together with either $R_{6a}$ or $R_{6c}$ may form a fused benzo, cycloalkyl, heterocyclo, or heteroaryl ring; or $R_{6c}$ taken together with $R_8$ may form a fused cycloalkyl or heterocyclo;

$R_9$ is selected from hydrogen, halogen, nitro, cyano, alkyl, substituted alkyl, alkenyl, substituted alkenyl, —$SR_{18}$, —$OR_{18}$, —$NR_{18}R_{19}$, —$CO_2R_{18}$, —$C(=O)R_{18}$, —$C(=O)NR_{18}R_{19}$, aryl, heterocyclo, cycloalkyl, and heteroaryl;

$R_{10}, R_{11}, R_{12}, R_{13}, R_{14}, R_{15}, R_{16}, R_{17}, R_{18}$, and $R_{19}$ (i) are selected independently of each other from hydrogen, alkyl, substituted alkyl, cycloalkyl, aryl, heteroaryl, and heterocyclo; or (ii) any two of $R_{10}, R_{11}, R_{12}, R_{13}, R_{14}, R_{15}, R_{16}, R_{17}, R_{18}$, and $R_{19}$ when attached to the same nitrogen atom may be taken together to form a heteroaryl or heterocyclo ring, with the remainder of $R_{10}, R_{11}, R_{12}, R_{13}, R_{14}, R_{15}, R_{16}, R_{17}, R_{18}$, and $R_{19}$ being selected independently from hydrogen, alkyl, substituted alkyl, cycloalkyl, aryl, heteroaryl, and heterocyclo;

$R_{11a}$, $R_{15a}$, and $R_{17a}$ are independently selected from alkyl, substituted alkyl, cycloalkyl, aryl, heteroaryl, and heterocyclo;

p is 1, 2, or 3; and q is 1, 2, or 3.

2. A compound according to claim 1, or a pharmaceutically-acceptable salt, hydrate, prodrug, or enantiomer thereof, wherein:

K is O;

Q is a —$CH_2$—;

Ar is phenyl optionally substituted one to three $R_{20}$;

$R_1$ is selected from hydrogen, $C_{1-6}$alkyl, —$C(=O)H$, —$C(=O)(C_{1-6}alkyl)$, —$CO_2H$, —$CO_2(C_{1-6}alkyl)$, or $C_{1-6}$alkyl substituted with one to two of hydroxy, —$O(C_{1-6}alkyl)$, —$C(=O)H$, —$C(=O)(C_{1-6}alkyl)$-$CO_2H$, —$CO_2(C_{1-6}alkyl)$, —$C(=O)NH_2$, —$C(=O)NH_2$, —$C(=O)NH(C_{1-4}alkyl)$, —$C(=O)N(C_{1-4}alkyl)_2$, —$NH_2$, —$NH(C_{1-4}alkyl)$, and —$N(C_{1-4}alkyl)_2$;

$R_2$ and $R_3$ are selected from halogen, $(C_{1-4})$alkyl, cyano, halo$(C_{1-4})$alkyl, halo$(C_{1-4})$alkoxy, nitro, phenyloxy, benzyloxy, and phenylthio;

$R_{20}$ at each occurrence is independently selected from halogen, $C_{1-4}$alkyl, hydroxy, $(C_{1-4})$alkoxy, halo$(C_{1-4})$alkyl, halo$(C_{1-4})$alkoxy, cyano, nitro, —$CO_2H$, —$C(=O)H$, —$CO_2(C_{1-4})$alkyl, —$C(=O)(C_{1-4})$alkyl, —$C(=O)NH(CH_2)_rCO_2H$, —$C(=O)NH(CH_2)_rCO_2(C_{1-4}alkyl)$, and $S(O)_2(C_{1-4}alkyl)$; or from phenyl, benzyl, phenyloxy, benzyloxy and heteroaryl in turn optionally substituted with one to two of halogen, $C_{1-4}$alkyl, hydroxy, $(C_{1-4})$alkoxy, halo$(C_{1-4})$alkyl, halo$(C_{1-4})$alkoxy, cyano, nitro, —$CO_2H$, —$C(=O)H$, —$CO_2(C_{1-4})$alkyl, and/or —$C(=O)(C_{1-4})$alkyl; or alternatively, two $R_{20}$ groups join together with each other to form a fused benzo ring; and r is 1, 2, 3, or 4.

3. A compound according to claim 2, or a pharmaceutically-acceptable salt, hydrate, prodrug, or enantiomer thereof, wherein $J_1$ is —$CHR_{6a}$—;

$J_2$ is —$CHR_{6b}$—;

$J_3$ is —$CHR_{6c}$—;

Y is $C(R_8)$;

$R_{6a}$, $R_{6b}$, $R_{6c}$ and $R_8$ are independently selected from a) hydrogen, halogen, and cyano;

b) —$SR_{16}$, —$OR_{16}$, —$NR_{16}R_{17}$, —$C(=O)R_{16}$, —$CO_2R_{16}$, —$C(=O)NR_{16}R_{17}$, —$NR_{16}C(=O)R_{17}$, —$NR_{16}C(=O)OR_{17}$, —$S(O)_qR_{17a}$, —$NR_{16}SO_2R_{17a}$, and —$SO_2NR_{16}R_{17}$; and c) $C_{1-4}$alkyl, phenyl, four to seven membered heterocyclo, $C_{3-7}$cycloalkyl, and five to six membered heteroaryl, each of which in turn is optionally substituted with one to two groups selected from $R_{22}$;

$R_{16}$ and $R_{17}$ are selected independently of each other from hydrogen, $C_{1-6}$alkyl, phenyl, four to seven membered heterocyclo, $C_{3-7}$cycloalkyl, and five to six membered heteroaryl, each of which in turn is optionally substituted with one to two groups selected from $R_{23}$;

$R_{17a}$ is $C_{1-6}$alkyl, phenyl, four to seven membered heterocyclo, $C_{3-7}$cycloalkyl, five to six membered heteroaryl each of which is optionally substituted with one to two groups selected from $R_{23}$; and $R_{22}$ and $R_{23}$ are at each occurrence selected independently from halogen, cyano, $C_{1-4}$alkyl, hydroxy, trifluoromethyl, trifluoromethoxy, —$O(C_{1-4}alkyl)$, —$C(=O)H$, —$C(=O)(C_{1-6}alkyl)$, —$CO_2H$, —$CO_2(C_{1-6}alkyl)$, —$C(=O)NH_2$, —$C(=O)NH_2$, —$C(=O)NH(C_{1-4}alkyl)$, —$C(=O)N(C_{1-4}alkyl)_2$, —$NH_2$, —$NH(C_{1-4}alkyl)$, —$N(C_{1-4}alkyl)_2$, hydroxy$(C_{1-4})$alkyl, methoxy$(C_{1-4})$alkyl, ethoxy$(C_{1-4})$alkyl, amino$(C_{1-4})$alkyl, and halo$(C_{1-4})$alkyl.

4. A compound according to claim 1, or a pharmaceutically-acceptable salt, hydrate, prodrug, or enantiomer thereof, wherein:

$R_1$ is hydrogen, $C_{1-6}$alkyl, —$C(=O)(C_{1-6}alkyl)$, or $C_{1-6}$alkyl substituted with one of —$C(=O)H$, —$C(=O)(C_{1-6}alkyl)$, —$CO_2H$, or —$CO_2(C_{1-6}alkyl)$.

5. A compound according to claim 1, or a pharmaceutically-acceptable salt, hydrate, prodrug, or enantiomer thereof, wherein Q-Ar together form:

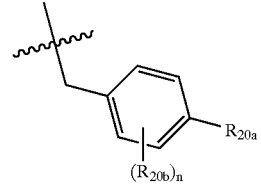

wherein $R_{20a}$ and $R_{20b}$ are independently selected from halogen, $C_{1-4}$alkyl, hydroxy, $(C_{1-4})$alkoxy, halo$(C_{1-4})$alkyl, halo$(C_{1-4})$alkoxy, cyano, nitro, —$CO_2H$, —$C(=O)H$, —$CO_2(C_{1-4})$alkyl, —$C(=O)(C_{1-4})$alkyl, —$C(=O)NH(CH_2)_rCO_2H$, —$C(=O)NH(CH_2)_rCO_2(C_{1-4}alkyl)$, and $S(O)_2(C_{1-4}alkyl)$; or from phenyl, benzyl, phenyloxy, benzyloxy and heteroaryl in turn optionally substituted with one to two of halogen, $C_{1-4}$alkyl, hydroxy, $(C_{1-4})$alkoxy, halo$(C_{1-4})$alkyl, halo$(C_{1-4})$alkoxy, cyano, nitro, —$NH_2$, —$NH(C_{1-4}alkyl)$, —$N(C_{1-4}alkyl)_2$, —$CO_2H$, —$C(=O)H$, —$CO_2(C_{1-4})$alkyl, and/or —$C(=O)(C_{1-4})$alkyl; or alternatively, two $R_{20b}$ groups join together with each other or one $R_{20b}$ joins together with $R_{20a}$ to form a fused benzo ring;

n is 0, 1, or 2; and r is 1, 2, 3, or 4.

6. A compound according to claim 1, or a pharmaceutically-acceptable salt, hydrate, prodrug, or enantiomer thereof, wherein $J_1$, $J_2$ and $J_3$ are each —$CH_2$—.

7. A compound according to claim 1, or a pharmaceutically-acceptable salt, hydrate, prodrug, or enantiomer thereof, wherein Y is CH.

8. A compound according to claim 1, or a pharmaceutically-acceptable salt, hydrate, prodrug, or enantiomer thereof, wherein $R_2$ and $R_3$ are both halogen.

9. A compound according to claim 1, or a pharmaceutically-acceptable salt, hydrate, prodrug, or enantiomer thereof, wherein Z is CH.

10. A compound having the formula (Ia),

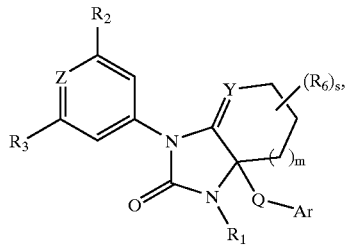

(Ia)

its enantiomers, diastereomers, or a pharmaceutically-acceptable salt, hydrate, solvate, or prodrug thereof, in which:

Q is —C(=O)— or —(CHR$_{4a}$)$_t$—

Ar is aryl or heteroaryl optionally substituted with one to three R$_{20}$;

Y is N or C(R$_8$);

Z is N or C(R$_9$);

R$_1$ is selected from hydrogen, C$_{1-6}$alkyl, —C(=O)H, —C(=O)(C$_{1-6}$alkyl), —CO$_2$H, —CO$_2$(C$_{1-6}$alkyl), or C$_{1-6}$alkyl substituted with one to two of hydroxy, —O(C$_{1-6}$alkyl), —C(=O)H, —C(=O)(C$_{1-6}$alkyl), —CO$_2$H, —CO$_2$(C$_{1-6}$alkyl), —C(=O)NH$_2$, —C(=O)NH$_2$, —C(=O)NH(C$_{1-4}$alkyl), —C(=O)N(C$_{1-4}$alkyl)$_2$, —NH$_2$, —NH(C$_{1-4}$alkyl), and —N(C$_{1-4}$alkyl)$_2$;

R$_2$ and R$_3$ are independently selected from halogen, (C$_{1-4}$)alkyl, cyano, halo(C$_{1-4}$)alkyl, halo(C$_{1-4}$)alkoxy, nitro, phenyloxy, benzyloxy, and phenylthio;

R$_{4a}$ is selected from hydrogen, OH, O(CH$_3$), O(CH$_2$CH$_3$), halogen, cyano, CF$_3$, OCF$_3$, NH$_2$, NH(CH$_3$), and N(CH$_3$)$_2$;

R$_6$ and R$_8$ at each occurrence are independently selected from (a) halogen, nitro, and cyano; or from (b) —SR$_{16}$, —OR$_{16}$, —NR$_{16}$R$_{17}$, —C(=O)R$_{16}$, —CO$_2$R$_{16}$, —C(=O)NR$_{16}$R$_{17}$, —NR$_{16}$C(=O)R$_{17}$, —NR$_{16}$C(=O)OR$_{17}$, —S(O)$_q$R$_{17a}$, —NR$_{16}$SO$_2$R$_{17a}$, and —SO$_2$NR$_{16}$R$_{17}$; or from (c) alkyl, alkenyl, aryl, heterocyclo, cycloalkyl, and heteroaryl, in turn optionally substituted with one to two groups selected from R$_{22}$; and/or (d) two R$_6$ groups taken together form keto (=O), with the remainder of the R$_6$ groups selected from (a), (b), and (c);

R$_9$ is selected from hydrogen, halogen, nitro, cyano, alkyl, substituted alkyl, alkenyl, substituted alkenyl, —SR$_{18}$, —OR$_{18}$, —NR$_{18}$R$_{19}$, —CO$_2$R$_{18}$, —C(=O)R$_{18}$, —C(=O)NR$_{18}$R$_{19}$, aryl, heterocyclo, cycloalkyl, and heteroaryl;

R$_{16}$ and R$_{17}$ are selected independently of each other from hydrogen, C$_{1-6}$alkyl, phenyl, four to seven membered heterocyclo, C$_{3-7}$cycloalkyl, and five to six membered heteroaryl, each of which in turn is optionally substituted with one to two groups selected from R$_{23}$;

R$_{17a}$ is C$_{1-6}$alkyl, phenyl, four to seven membered heterocyclo, C$_{3-7}$cycloalkyl, five to six membered heteroaryl each of which is optionally substituted with one to two groups selected from R$_{23}$;

R$_{20}$ at each occurrence is selected from halogen, C$_{1-6}$alkyl, hydroxy, (C$_{1-4}$)alkoxy, (C$_{1-4}$)alkylthio, cyano, nitro, —CO$_2$H, —C(=O)H, —CO$_2$(C$_{1-4}$alkyl), —C(=O)(C$_{1-4}$)alkyl, —C(=O)NH(CH$_2$)$_r$CO$_2$H, —C(=O)NH(CH$_2$)$_r$CO$_2$(C$_{14}$alkyl), S(O)$_2$(C$_{1-4}$alkyl), phenyl, benzyl, phenyloxy, benzyloxy, five to six membered heteroaryl, C$_{3-7}$cycloalkyl, and four to seven membered heterocyclo, wherein each of the alkyl, alkoxy, and cyclic groups in turn are optionally substituted with one to three of R$_{24}$;

R$_{22}$, R$_{23}$ and R$_{24}$ are at each occurrence selected independently from halogen, cyano, nitro, C$_{1-6}$alkyl, hydroxy, trifluoromethyl, trifluoromethoxy, —O(C$_{1-6}$alkyl), —C(=O)H, —C(=O)(C$_{1-6}$alkyl), —CO$_2$H, —CO$_2$(C$_{1-6}$alkyl), —C(=O)NH$_2$, —C(=O)NH$_2$, —C(=O)NH(C$_{1-4}$alkyl), —C(=O)N(C$_{1-4}$alkyl)$_2$, —NH$_2$, —NH(C$_{1-4}$alkyl), —N(C$_{1-4}$alkyl)$_2$, hydroxy(C$_{1-4}$)alkyl, methoxy(C$_{1-4}$)alkyl, ethoxy(C$_{1-4}$)alkyl, amino(C$_{1-4}$)alkyl, and halo(C$_{1-4}$)alkyl;

m is 1;

p and q are independently 1, 2, or 3;

r and s are 0, 1, 2, 3 or 4; and t is 0, 1 or 2.

11. A compound according to claim 10 having the formula,

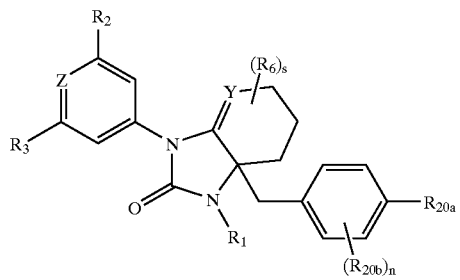

or a pharmaceutically acceptable salt, hydrate, solvate, or prodrug thereof, in which:

R$_{20a}$ and R$_{20b}$ are independently selected from halogen, C$_{1-4}$alkyl, hydroxy, (C$_{1-4}$)alkoxy, halo(C$_{1-4}$)alkyl, halo(C$_{1-4}$)alkoxy, cyano, nitro, —CO$_2$H, —C(=O)H, —CO$_2$(C$_{1-4}$)alkyl, —C(=O)(C$_{1-4}$)alkyl, C(=O)NH(CH$_2$)$_r$CO$_2$H, —C(=O)NH(CH$_2$)$_r$CO$_2$(C$_{1-4}$alkyl), and S(O)$_2$(C$_{1-4}$alkyl); or from phenyl, benzyl, phenyloxy, benzyloxy and heteroaryl in turn optionally substituted with one to two of halogen, C$_{1-4}$alkyl, hydroxy, (C$_{1-4}$)alkoxy, halo(C$_{1-4}$)alkyl, halo(C$_{1-4}$)alkoxy, cyano, nitro, —NH$_2$, —NH(C$_{1-4}$alkyl), —N(C$_{1-4}$alkyl)$_2$, —CO$_2$H, —C(=O)H, —CO$_2$(C$_{1-4}$)alkyl, and/or —C(=O)(C$_{1-4}$)alkyl; or alternatively, two R$_{20b}$ groups join together with each other or one R$_{20b}$ joins together with R$_{20a}$ to form a fused benzo ring; and n is 0, 1 or 2.

12. A compound according to claim 11, or a pharmaceutically-acceptable salt, hydrate, prodrug, or enantiomer thereof, in which R$_1$ is C$_{1-4}$ alkyl.

13. A compound according to claim 11, or a pharmaceutically-acceptable salt, hydrate, prodrug, or enantiomer thereof, in which R$_2$ and R$_3$ are both halogen.

14. A compound according to claim 11, or a pharmaceutically-acceptable salt, hydrate, prodrug, or enantiomer thereof, in which R$_{20a}$ is cyano or halogen.

15. A compound according to claim 11, or a pharmaceutically-acceptable salt, hydrate, prodrug, or enantiomer thereof, having the formula,

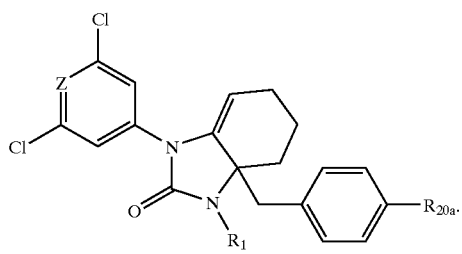

16. A compound according to claim 15, or a pharmaceutically-acceptable salt, hydrate, prodrug, or enantiomer thereof, in which Z is CH, $R_1$ is methyl or ethyl, and $R_{20a}$ is cyano or halogen.

17. A pharmaceutical composition comprising at least one compound according to claim 1 and a pharmaceutically acceptable carrier or diluent.

18. A pharmaceutical composition comprising at least one compound according to claim 10 and a pharmaceutically acceptable carrier or diluent.

19. A method of treating a LFA-1/ICAM-associated condition in a mammal comprising administering to the mammal a therapeutically-effective amount of a compound according to claim 1 wherein the LFA-1/ICAM-associated condition is selected from acute or chronic graft-versus-host reactions, acute or chronic transplant rejection, multiple sclerosis, rheumatoid arthritis, osteoarthritis, diabetes, inflammatory bowel disease, Crohn's disease, reperfusion injury, psoriasis, asthma, chronic obstructive pulmonary disease (COPD), and systemic lupus erythematosus.

20. The method of claim 19 in which the LFA-1/ICAM-associated condition is selected from acute or chronic graft versus host reactions, acute or chronic transplant rejection, rheumatoid arthritis, psoriasis and chronic obstructive pulmonary disease.

* * * * *